US009745362B2

(12) United States Patent
An et al.

(10) Patent No.: US 9,745,362 B2
(45) Date of Patent: Aug. 29, 2017

(54) SEED-SPECIFIC EXPRESSION VECTOR AND ITS CONSTRUCTION METHODS AND APPLICATIONS

(75) Inventors: Shengjun An, Shijiazhuang (CN); Xiqing Chai, Shijiazhuang (CN); Kunsheng Wang, Beijing (CN); Tiemei Shao, Shijiazhuang (CN); Zhan Jiao, Shijiazhuang (CN); Xin Wen, Shijiazhuang (CN); Xue Li, Shijiazhuang (CN); Pei Liu, Shijiazhuang (CN); Haigang Lu, Shijiazhuang (CN); Yunyu Chen, Shijiazhuang (CN); Liangyuan Hu, Beijing (CN); Haimin Xu, Beijing (CN); Chenggang Yu, Beijing (CN)

(73) Assignees: Shengjun An, Hebei (CN); Kunsheng Wang, Beijing (CN); Xiqing Chai, Hebei (CN)

( * ) Notice: Subject to any disclaimer, the term of this patent is extended or adjusted under 35 U.S.C. 154(b) by 901 days.

(21) Appl. No.: 13/515,209

(22) PCT Filed: Dec. 9, 2010

(86) PCT No.: PCT/CN2010/079620
§ 371 (c)(1),
(2), (4) Date: Jun. 11, 2012

(87) PCT Pub. No.: WO2011/069459
PCT Pub. Date: Jun. 16, 2011

(65) Prior Publication Data
US 2012/0288893 A1 Nov. 15, 2012

(30) Foreign Application Priority Data
Dec. 9, 2009 (CN) .......................... 2009 1 0250703

(51) Int. Cl.
*C07K 14/775* (2006.01)
*C12N 15/82* (2006.01)

(52) U.S. Cl.
CPC ........ *C07K 14/775* (2013.01); *C12N 15/8257* (2013.01)

(58) Field of Classification Search
None
See application file for complete search history.

(56) References Cited

U.S. PATENT DOCUMENTS

| 5,445,947 A * | 8/1995 | Metz ..................... C12N 9/0008 435/134 |
| 5,643,757 A * | 7/1997 | Malik et al. .................. 435/69.7 |
| 6,288,304 B1 * | 9/2001 | Moloney et al. ............. 800/288 |
| 7,786,352 B2 | 8/2010 | Moloney et al. |
| 2005/0172359 A1 * | 8/2005 | Moloney et al. ............. 800/281 |
| 2006/0179514 A1 * | 8/2006 | Rooijen ............. C12N 15/8257 800/281 |
| 2007/0292918 A1 * | 12/2007 | Stelman et al. ............. 435/69.1 |

FOREIGN PATENT DOCUMENTS

| CN | 101037692 | 9/2007 |
| WO | WO 98/18948 | 5/1998 |
| WO | WO 01/16340 | 3/2001 |
| WO | WO0250289 | 6/2002 |
| WO | WO 2005/047455 | 5/2005 |
| WO | WO2005047455 | 5/2005 |
| WO | WO2008017906 | 2/2008 |

OTHER PUBLICATIONS

EF695401 (published Jul. 22, 2007).*
GenBank M63985.1 (published Apr. 27, 1993).*
Plant et al (Plant Molecular Biology, 25, pp. 193-205, 1994).*
http://www.kazusa.or.jp/codon/cgi-bin/showcodon.cgi?species=4232 (published online Dec. 4, 2007; see appended image capture).*
Chow (Journal of Experimental Microbiology and Immunology, 2005, 8:8-13).*
Rohila et al (The Plant Journal, 2004, 38: 172-181).*
PCT/CN2010/079620, Search Report mailed Mar. 17, 2011, 3 pages—Chinese, 5 pages—English.
Hong HP, Ross JH, Gerster JL, Rigas S, Datla RS, Hatzopoulos P, Scoles G, Keller W, Murphy DJ, Robert LS. Promoter sequences from two different brassica napus tapetal oleosin-like genes tapetal expression of β-glucuronidase in transgenic brassica plants, Plant Mol Biol. Jun. 1997;34(3):549-555.
Plant AL, van Rooijen GJ, Anderson CP, Moloney MM. Regulation of an arabidopsis oleosin gene promoter in transgenic brassica napus, Plant Mol Biol. May 1994;25(2):193-205.
Nykiforuk C.L , Boothe J.G , Murray E.W , Keon R.G , Goren H.J, Markley N.A. and Moloney M.M. Transgenic expression and recovery of biologically active recombinant human insulin from Arabidopsis thaliana seeds [J] . Plant Biotechnol, 2006, 4: 77-85.
Reda Helmy Sammour. Proteins of linseed extraction and characterization by electrophoresis,Botanical Bulletin of Academia Sinica,1999,40,121-126.
Borgmeyer JR, Smith CE, Huynh QK.Isolation and characterization of a 25kDa antifugal protein from flax seeds. Biochem Biophys Res Commun. 1992 ,187(1):480-487.

(Continued)

*Primary Examiner* — Cathy Kingdon Worley
*Assistant Examiner* — Stephen Uyeno
(74) *Attorney, Agent, or Firm* — Andrew F. Young, Esq.; Lackenbach Siegel, LLP

(57) ABSTRACT

A seed-specific expression vector and its construction methods and applications are disclosed. A fusion protein expression cassette consisting of *Arachis hypogaea* oleosin gene-apolipopoprotein A-$I_{Milano}$ (A-IM) gene driven by *Brassica napus* oleosin gene promoter is inserted between the HindIII and SacI sites of a plant binary expression vector pBI121, obtaining the plant expression vector pBINOA of the invention. In addition, a method for producing apolipoprotein A-$I_{Milano}$ is provided, in which the expression vector is used to transform oil sunflower which is used as a plant bioreactor. The method can not only improve the yield of apolipoprotein A-$I_{Milano}$, but also greatly reduce production costs, and is suitable for industrial production.

8 Claims, 6 Drawing Sheets

(56) References Cited

OTHER PUBLICATIONS

Cory L. Nykiforukl, Yin Shenl, Elizabeth W. Murray, Joseph G. Boothel, David Busseuil,Eric Rhe' aurae, Jean-Claude Tardif, Alexandra Reid and Maurice M. Moloney. Expression and recovery of biologically active recombinant Apolipoprotein AIMilano from transgenic safflower (Carthamus tinctorius) seeds. Plant Biotechnology Journal (2010), pp. 1-14.

Transgenic expression and recovery of biologically active recombinmant human insulin from Arabidopsis thaliana seeds, by Nykiforuk, Boothe, Murray, Keon, Goren, Markley and Moloney, Plant Biotechnology Journal (2006), pp. 77-85. © 2005 Blackwell Publishing Ltd., Jul. 12, 2005.

\* cited by examiner

SEED-SPECIFIC EXPRESSION VECTOR AND ITS CONSTRUCTION METHODS AND APPLICATIONS

CROSS REFERENCE TO RELATED APPLICATIONS

This application relates to and claims priority from PCT/CN2010/079620 filed Dec. 9, 2010, the entire contents of which are incorporated herein by reference, and which further claims priority from CH Ser. No. 200910250703.9 filed Dec. 9, 2009.

FIELD OF THE INVENTION

The present invention is directed to a seed-specific expression vector and its construction methods and applications, and in particular to a seed-specific expression vector and its construction methods and a method for producing apolipoprotein A-I-$_{Milano}$ (AIM) in oil sunflower with this vector.

BACKGROUND OF THE INVENTION

Cardiovascular disease (CVD) is the leading cause of human deaths worldwide. It is estimated that, by 2015, approximately 20 million people will die from cardiovascular disease (CVD). Numerous cardiovascular diseases (CVDs) (such as myocardial infarction and apoplexy) are the leading complications of atherosclerosis (AS). So far, the pathogenesis of atherosclerosis has not been fully understood. Abnormal lipid metabolism is one of the main risk factors that cause this disease. High-level of low density lipoprotein (LDL) and low-level of high density lipoproteins (HDL) are the two most important risk factors. Traditional strategies of treatment are to reduce the content of total cholesterol (TC) and low density lipoproteins cholesterol (LDL-C) in blood plasma. Statins are the preferred lipid-lowering drug at present. However, they cannot eliminate existing plaques deposited on artery wall, or fundamentally cure atherosclerosis (AS). More and more scientists in different countries have turn to the other risk factor, low-level of high density lipoprotein (HDL). Epidemiological studies indicate that, the level of high density lipoproteins (HDL) in blood plasma is in negative correlation to the incidence of coronary diseases. It is believed that high density lipoprotein contributes to the prevention of atherosclerosis. Treating atherosclerosis through improving the level of high density lipoprotein is a new approach for treating acute coronal atherosclerosis diseases that is emerging in pharmaceutical industry. It is called high density lipoprotein targeted therapy. Apolipoprotein A-I (apo A-I) is the main proteic component of high density lipoproteins. Apolipoprotein A-I is synthesized in liver and small intestine. The primary translation product is the preproprotein (preproapo A-I) containing 267 amino acid residues. Preproprotein is then processed into the proprotein (proapo A-I), through the cleavage of an octadeca peptide by signal peptidase. The proapo is secreted and processed into mature plasma apolipoprotein A-I through cleavage of a hexapeptide (Arg-His-Phe-Trp-Gln-Gln) by specific extracellular converting enzymes. The mainly mechanism of action of apolipoprotein A-I is to promote the cholesterol efflux, antioxidation, and to decrease platelet aggregation.

Apolipoprotein (apolipoprotein A-IM, apoA-IM) is a natural mutant of apolipoprotein A-I (Arg173-Cys). Compared with apolipoprotein A-I, the loss of Arg173 leads to the reduction of content of α-helix and the enhancement of the capability to bind lipid. Apolipoprotein A-I-$_{Milano}$ tends to form a dimer (A-IM/A-IM). This dimer stimulates the reverse transport of cholesterol, and thus the clearance of cholesterol, more efficiently than apolipoprotein A-I. Compared with apolipoprotein A-I, apolipoprotein A-I-$_{Milano}$ more efficiently decrease the oxidation of low density lipoprotein. At present, apolipoprotein A-I-$_{Milano}$ is the only pharmaceutical protein that is shown to remove the thrombus deposited on artery wall, with broad application prospect.

It is reported in the Journal of the American Medical Association (JAMA) recently that, apolipoprotein A-I-$_{Milano}$ effects changes of artery atherosclerosis lesion with unprecedentedly speed and amplitude and little side effect. With various application prospects, it has become the focus of pharmaceutical research and industrial competition worldwide. Pfizer, the largest pharmaceutical company in the world, estimates that any drug reversing artery plaque may be a billion dollar business. Therefore, the development of apolipoprotein A-I-$_{Milano}$ will definitely bring about enormous economical and social benefits, as well as enhance the competitive strength in the field of drug development against cardiovascular diseases and atherosclerosis diseases.

In addition, data obtained from small-scale clinical trials reveal that the clinical dosage of apolipoprotein A-I is 5-6 g per treatment course. The high therapeutic dosage of apolipoprotein A-I and the high prevalence of atherosclerosis suggest huge market demand and also an opportunity for the development of apolipoprotein A-I-$_{Milano}$. At present, apolipoprotein A-I-$_{Milano}$ is produced by Eperion, US by means of biosynthesis, which is of high cost and low yield and undesirable for large-scale production. The recombinant expression of the protein in bacterial system is generally attractive. However, the yield is low, and *Escherchia coli* endotoxin tends to form tight complex with apolipoprotein A-I-$_{Milano}$. Besides, the protein purification method is expensive and poor in safety. Therefore, there is the need for a method of producing apolipoprotein A-I-$_{Milano}$ with high yield and efficiency.

Plant bioreactor, also called molecular medicine farming, refers to the large-scale production of heterologous proteins of importance and commercial value, especially medical proteins used for the treatment or diagnosis of diseases, by a plant biological system. Mammalian antibodies were successfully expressed in transgenic plants for the first time in 1989. Both the heavy and light chains were expressed and correctly assembled in transgenic tobacco, demonstrating for the first time the possibility to use plant as a bioreactor. Since then, researches directed to transgenic plants have been rising. Many other medical proteins have been expressed in different plants sooner or later, such as hirudin, interferon, human albumin, and functional antibodies. Plants already used in plant bioreactor research include tobacco, *Arabidopsis thaliana*, soybean, wheat, rice, rape, potato and tomato, etc.

SemBioSys Genetic, Inc, a Canadian biotechnology company developing protein drug combinations for metabolic and cardiovascular diseases, filed a patent application in China (CN1906296A) regarding the method for producing apolipoprotein A-I and apolipoprotein A-I-$_{Milano}$ with transgenic *Carthamus tinctorius* and *Arabidopsis thaliana*, in which a chimeric nucleic acid construct is introduced into *Arabidopsis thaliana* or *Carthamus tinctorius*. Apolipoprotein A-I and apolipoprotein A-I-$_{Milano}$ is expressed in seeds upon seed setting. *Arabidopsis thaliana* is an annual or biennial herb. It has the smallest genome among all plants.

Due to its high generic homozygosity, high mutation rates may be achieved upon physical or chemical treatments, providing various metabolic deficiency phenotypes. Thus *Arabidopsis thaliana* represents a good material for genetics research, and is called "the fruit fly of the plant world". Though *Arabidopsis thaliana* is widely used in experimental contexts, it is not utilized in large-scale production. *Carthamus tinctorius* is an annual herb. Its seed can be used for oil extraction, and thus it is an important oil crop. It is distributed in the temperate zone. In China, it is mainly distributed in the Northwest (in particular Xinjiang and Tibet), and then North China and Northeast regions. *Carthamus tinctorius* suffers from the disadvantage of relatively low yield per mu (120-150 kg) and suboptimal oil content of the achene (34~55%), resulting in low productivity of the end product protein and a high cost.

Therefore, there is still the need for a method for producing apolipoprotein A-I and apolipoprotein A-I-$_{Milano}$ with stable and high yield, low cost, and simple procedures.

BRIEF DESCRIPTION OF THE INVENTION

The inventor, upon extensive investigation and creative work, accomplished the invention by stably and high-efficiently producing apolipoprotein A-I and apolipoprotein A-I-$_{Milano}$ through the construction of a specific expression vector and utilizing oil sunflower as bioreactor.

The present invention is directed to a method for producing apolipoprotein A-I or apolipoprotein A-I-$_{Milano}$ by recombinant DNA technology, in particular a method for producing apolipoprotein A-I or apolipoprotein A-I-$_{Milano}$ using oil sunflower as the host. Specifically, the invention involves the expression of the gene of a fusion protein consisting of *Arachis hypogaea* oleosin and apolipoprotein A-I or apolipoprotein A-I-$_{Milano}$ in oil sunflower oil body, thereby producing the important drugs apolipoprotein A-I and apolipoprotein A-I-$_{Milano}$ preferably apolipoprotein A-I-$_{Milano}$, used for treating atherosclerosis and the related cardiovascular diseases.

In one aspect, the invention provides a seed-specific expression vector comprising apolipoprotein A-I-$_{Milano}$ gene fused with *Arachis hypogaea* oleosin gene or apolipoprotein A-I gene fused with *Arachis hypogaea* oleosin gene, preferably apolipoprotein A-I-$_{Milano}$ gene fused with *Arachis hypogaea* oleosin gene, in which the promoter of the said vector is the *Brassica napus* oleosin gene promoter. The above vector is used for producing apolipoprotein A-I or apolipoprotein A-I-$_{Milano}$, preferably apolipoprotein A-I-$_{Milano}$ in oil sunflower.

In another aspect, the invention provides a method for the construction the above high-efficient seed-specific expression vector, including the following steps:

1) Isolating and cloning of *Brassica napus* oleosin gene promoter and *Arachis hypogaea* oleosin gene;

2) Designing and synthesizing an apolipoprotein A-I-$_{Milano}$ gene or apolipoprotein A-I gene according to the codon preference of the plant;

3) Constructing a plant expression vector in which the fusion of *Arachis hypogaea* oleosin gene with apolipoprotein A-I-$_{Milano}$ or apolipoprotein A-I gene is driven by *Brassica napus* oleosin gene promoter.

The details of the steps are explained as follows:

1) Isolating and cloning of *Brassica napus* oleosin gene promoter and *Arachis hypogaea* oleosin gene: The 20 kD oleosin gene promoter is amplified by PCR from *Brassica napus* genome DNA, and cloned into pUC19 (purchased from MBI), obtaining a recombinant plasmid pUCN. The *Arachis hypogaea* oleosin gene lacking the stop codon is amplified by PCR using *Arachis hypogaea* genome DNA as template. The specific rape variety may be one that is published or used in the art, such as Qingyou 14, Hufeng 101, cold-resistance king of high oil, Early Oil 100-Day, Qingyou 2, etc., preferably Qingyou 14. The *Brassica napus* oleosin gene promoter may be cloned between the appropriate sites of pUC19, and preferably between the HindIII and BamHI sites of pUC19. The *Arachis hypogaea* variety may be one that is already published or used in the art, such as Jihua 4, Jiyou 7, Baisha, Luhua 11, Haihua, Fenghua 1, etc., preferably jihua 4.

2) Designing and synthesizing an apolipoprotein A-I-$_{Milano}$ gene or apolipoprotein A-I gene according to the codon preference of the plant: This is to optimize apolipoprotein A-I-$_{Milano}$ or apolipoprotein A-I gene (preferably the former) according to the codon usage of *Helianthus* animus. All codons with the usage frequency of less than 10% shall be regarded as rare codons and thus abolished, while the remaining codons shall be optimized according to the frequency of *Helianthus annuus* codon usage. The molecular weight of gene before optimization is 451.4. The sequence identity of the sequences before and after optimization is higher than 60%, preferably higher than 65%, even preferably higher than 72%. The preferable molecular weight of gene after optimization is 451.3. For the usage frequency of *Helianthus annuus* codons, reference may be made to http://www.kazusa.or.jp/codon/cgi-bin/showcodon.cgi?species=4232.

3) Constructing a plant expression vector in which the fusion of *Arachis hypogaea* oleosin gene with apolipoprotein A-I-$_{Milano}$ or apolipoprotein A-I gene is driven by *Brassica napus* oleosin gene promoter: The fusion gene of *Arachis hypogaea* oleosin gene with apolipoprotein A-I-$_{Milano}$ gene or apolipoprotein A-I gene is constructed by overlapping PCR. Preferably, *Arachis hypogaea* oleosin gene is fused with apolipoprotein A-I-$_{Milano}$ gene, obtaining the fusion gene Ole/apoA-I$_M$. The fusion gene is linked into pUCN, preferable between the BamHI and SacI sites, obtaining recombinant plasmid pUCNOA. The recombined plasmid pUCNOA is subjected to double digestion, preferably with HindIII and SacI, to recover the exogenous fragment of 2202 bp. The exogenous fragment is subsequently inserted between the HindIII and SacI of pBI121, a binary plant expression vector commonly used in plant transgenic engineering, obtaining pBINOA, the plant expression vector in which the fusion gene of *Arachis hypogaea* oleosin with apolipoprotein A-I-$_{Milano}$ is driven by *Brassica napus* oleosin gene promoter, or in which the fusion gene of *Arachis hypogaea* oleosin gene with apolipoprotein A-I is driven by *Brassica napus* oleosin gene promoter.

In another aspect, the invention provides a method for producing apolipoprotein A-I-$_{Milano}$ or apolipoprotein A-I with the above seed-specific plant expression vectors, including the following steps:

1) introducing the above construction expression vectors into an explant of a receptor plant;

2) cultivating the above receptor plant materials into a complete plant and obtain seeds thereof;

3) isolating apolipoprotein A-I-$_{Milano}$ or apolipoprotein A-I from the seeds.

Preferably, the receptor plant is oil sunflower. Preferably, apolipoprotein A-I-$_{Milano}$ is produced.

The specific procedures include the following details.

1) A seed-specific plant expression vector carrying apolipoprotein A-I-$_{Milano}$ gene or apolipoprotein A-I gene is introduced into the explant of a oil sunflower restoring line. The method for introducing the seed-specific plant expression vector into the restoring line of oil sunflower may be a conventional introduction method in the art, including but not limited to gene gun bombardment, pollen-tube pathway, ovary injection, and *Agrobacterium*-mediated transformation, preferably *Agrobacterium*-mediated transformation. In *Agrobacterium*-mediated transformation, the seed-specific plant expression vector carrying apolipoprotein A-I-$_{Milano}$ gene or apolipoprotein A-I gene is introduced into *Agrobacterium*, which mediates the transformation of the explants of the restoring line of oil sunflower. The explants include shoot apexes excised from sterile seedling, cotyledon, cotyledon node, and seedlings with one cotyledon detached. Preference is made to seeding plant stripped of one cotyledon.

2) Resistance seedling is obtained through resistance selection of the regenerated plants obtained after transgenesis, and is transplanted into greenhouse after rootage for cultivation until maturity to harvest seeds. The resistance seedling is transplanted into greenhouse after taking root for vermiculite and nutritional soil mixture cultivation. PCR test and southern blotting test shall be conducted during the Seedling Stage. Western blotting test shall be conducted after harvest against the fusion protein of oleosin and apolipoprotein A-I-$_{Milano}$;

3) The seed containing apolipoprotein A-I-$_{Milano}$ or apolipoprotein A-I is ground in buffer solution. The oil body is separated from other components of the seed by centrifugation and washed. Apolipoprotein A-I-$_{Milano}$ or apolipoprotein A-I is released from the oil body surface through digestion, purified by HPLC, and subjected to identification.

In the vector and method of the invention, *Brassica* lupus oleosin promoter is used. Experimental research indicates that this promoter can greatly improve the expression efficiency of apolipoprotein A-I-$_{Milano}$ gene. Preferably, Kozak consensus sequence may be positioned near the initiator codon of oleosin gene, further improving the expression efficiency.

In the vector and method of the invention, the apolipoprotein A-I-$_{Milano}$ or apolipoprotein A-I is expressed as fusion protein with oleosin. The protein of interest is specifically expressed in transgenic plants in the oil body as fusion with oleosin. Taking advantage of the hydrophobic/lipophilic characteristic of the oil body, the seeds of the transgenic plant is subjected to grind, extraction, centrifugation, and recovery of the upper oil phase, thereby separating the fusion protein from other components in the cell. More than 90% of seed proteins can be removed. Preferably, a thrombin recognition site is positioned between oleosin and apolipoprotein A-I-$_{Milano}$ or apolipoprotein A-I for releasing apolipoprotein A-I-$_{Milano}$ from oil body, thereby simplifying the purification process of the expression product and improving the purification efficiency. The preferred oleosin is *Arachis hypogaea* oleosin. The fusion expression of *Arachis hypogaea* oleosin and apolipoprotein A-I-$_{Milano}$ or apolipoprotein A-I is optimal in terms of quality and quantity.

In the vector and method of this invention, in order to improve the expression efficiency of apolipoprotein A-I-$_{Milano}$ gene or apolipoprotein A-I gene, the apolipoprotein A-I-$_{Milano}$ gene or apolipoprotein A-I gene is optimized according to apolipoprotein A-I-$_{Milano}$ or apolipoprotein A-I gene sequence, the preference of codon usage of *Helianthus annuus* and GC content, and is fully synthetic.

In the methods of apolipoprotein A-I-$_{Milano}$ or apolipoprotein A-I production disclosed by this invention, the preferable plant bioreactor is oil sunflower. As an important oil crop in China, oil sunflower has a long planting history and irreplaceable advantages relative to other crops. With high yield and as a drought tolerance crop, oil sunflower can be planted in severe environment such as alkali soils, arid areas, and even in deserts. It is therefore suitable for large-scale planting. The planting of oil sunflower does not conflict with alimentary crops, and is beneficial in terms of improving the utilization of mountain ridges and dry and unfruitful area, alleviating the insufficiency of cultivated land. Therefore, it is particularly beneficial in China to use oil sunflower as bioreactor for the large-scale production of apolipoprotein A-I-$_{Milano}$. A most significant advantage is the greatly improved production efficiency and productivity achieved by oil sunflower as bioreactor, compared with prior art methods using *Carthamus tinctorius* as the bioreactor for the production of apolipoprotein A-I-$_{Milano}$ or apolipoprotein A-I.

The following advantages are achieved by the method of producing apolipoprotein A-I-$_{Milano}$ of the invention.

1. The heterologous protein expressed in plant is similar to the protein expressed in mammals and can be correctly fold. This is of particular importance for the production of medical proteins with in vivo activity.

2. The apolipoprotein A-I-$_{Milano}$ produced in plant bioreactor is safer, because it avoids the contamination of *E. coli* endoxin or pathogens.

3. The oil body expression system of transgenic plant used for expressing apolipoprotein A-I-$_{Milano}$ greatly simplifies the purification process, reduces cost, and facilitates the industrialization, compared with *Arabidopsis thaliana* and *Carthamus tinctorius* systems already adopted by SemBioSys Genetics.

4. The seed-specific plant expression vector and preparation method introduced by this invention can greatly improve the expression quantity of apolipoprotein A-I-$_{Milano}$ or apolipoprotein A-I, which can reach 1.5% of the total protein content of seed.

5. *Agrobacterium*-mediated transformation is used, which not only reduce cost and improves transformation efficiency, but also improves the genetic stability of the transgenic plant.

This invention utilizes transgenic technology to develop a high expression efficiency plant bioreactor. The resultant product, apolipoprotein A-I-$_{Milano}$ or apolipoprotein A-I, is an potent drug for the treatment of cardiovascular diseases and atherosclerosis diseases.

Definitions:

Unless specially defined otherwise, all terms referred in this invention shall have the common meanings in the field, wherein the meaning of abbreviations are provided as follows:

LDL: Low density lipoprotein (LDL)
HDL: High density lipoproteins (HDL)
TC: Total cholesterol (TC) in blood plasma
LDL-C: Low density lipoproteins cholesterol (LDL-C)
apoA-I: Apolipoprotein A-I
apoA-IM: Apolipoprotein A-I-$_{Milano}$ (AIM)
A-IM/A-IM: apolipoprotein A-I-$_{Milano}$ dimer
pUC19: a common *E. coli* cloning vector, obtained from MBI
pBI121: a common plant expression vector in plant transgenic engineering
pUCN: pUC19 vector carrying *Brassica napus* oleosin promoter (NOP) inserted between the HindIII and BamHI sites Ole/apoA-IM: Fusion gene of *Arachis hypogaea* oleosin with apolipoprotein A-I-$_{Milano}$ pUCNOA: pUC19 vector carrying the fusion gene of *Brassica napus* oleosin gene promoter (NOP), *Arachis hypogaea* oleosin gene and apolipoprotein A-I-$_{Milano}$, inserted between the HindIII and SacI sites pBINOA: pBI121 vector carrying the fusion gene of *Brassica napus* oleosin promoter (NOP), *Arachis hypogaea* oleosin gene and apolipoprotein A-I-$_{Milano}$, inserted between the HindIII and SacI sites.

DETAILED DESCRIPTION OF THE INVENTION

The following embodiments are provided for further description of this invention, and are not construed as limiting to the scope of the invention. Given the present disclosure, alterations may be made to this invention without departing from the spirit of this invention. All these alterations are within the scope of the present invention.

Unless otherwise specified, the methods referred to in the following embodiments are practiced according to general practice in this field.

Example 1: Seed-Specific Plant Expression Vector

Figure 1:
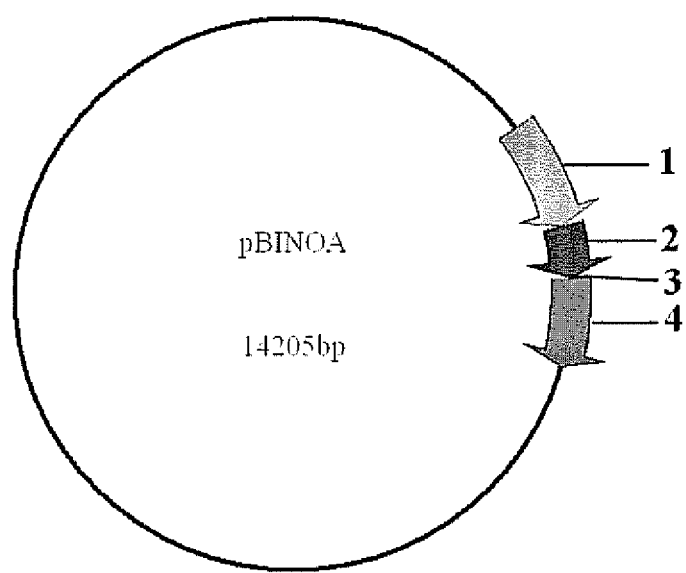
FIG. 1 Schematic Drawing of the Seed-specific plant expression vector pBINOA.

*Brassica napus* oleosin gene promoter (NOP) was amplified by PCR, inserted into pUC19 between the HindIII and BamHI sites, obtaining pUCN. Apolipoprotein gene was designed according to apolipoprotein A-I-$_{Milano}$ (AIM) gene sequence and the codon usage of *Helianthus annuus*, synthetically produced, and inserted at the 3' end of the *Arachis hypogaea* oleosin gene (Ole), obtaining the fusion gene of *Arachis hypogaea* oleosin and apolipoprotein A-I-$_{Milano}$. Thrombin cleavage site was added between the *Arachis hypogaea* oleosin gene and the apolipoprotein A-I-$_{Milano}$ gene. The fusion gene was inserted into pUCN between the BamHI and SacI sites to obtain pUCNOA. pUCNOA was double digested with HindIII and SacI. The 2202 bp exogenous fragment was collected on agarose gel, and inserted between the and SacI sites of plant binary expression vector pBI121, obtaining the plant expression vector pBINOA of the invention. The expression cassette of pBINOA is the Ole/apoA-I$_M$ fusion gene driven by *Brassica napus* oleosin promoter. The structure of pBINOA is shown in FIG. 1. 1: *Brassica napus* oleosin gene promoter; 2: *Arachis hypogaea* oleosin gene; 3: thrombin cleavage site; 4: apolipoprotein A-I-$_{Milano}$ gene. By sequencing of pBINOA, the sequence of the expression cassette is obtained as shown in SEQ ID NO: 15, with the length of 2202 bp.

Example 2: Construction of Seed-Specific Plant Expression Vector pBINOA

Figure 2:
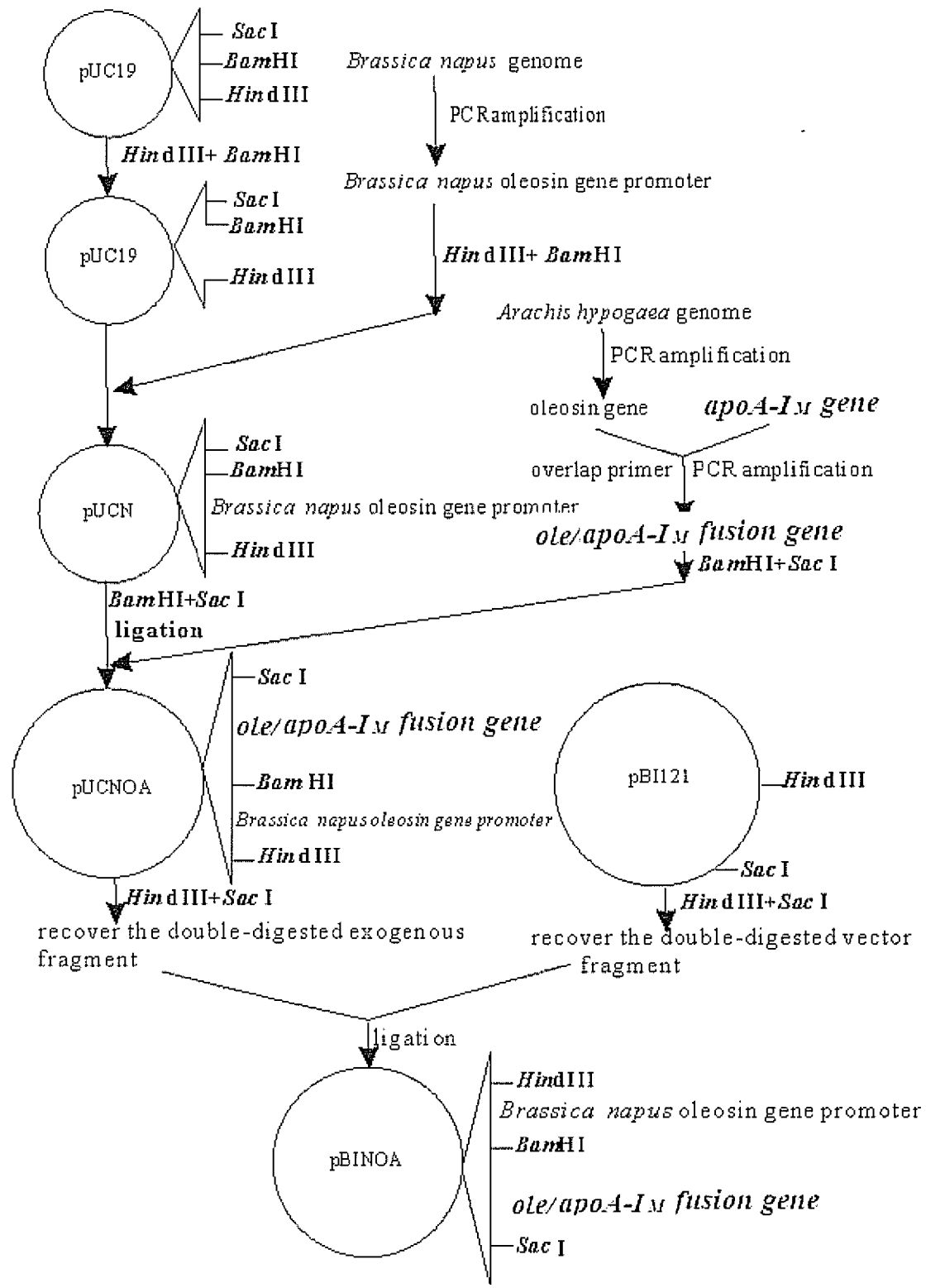
FIG. 2 Schematic Drawing of the Construction Process of Seed-specific plant expression vector pBINOA.

The construction of the plant expression vector pBINOA is shown in FIG. 2. The specific procedures are provided as follows.

Figure 3:
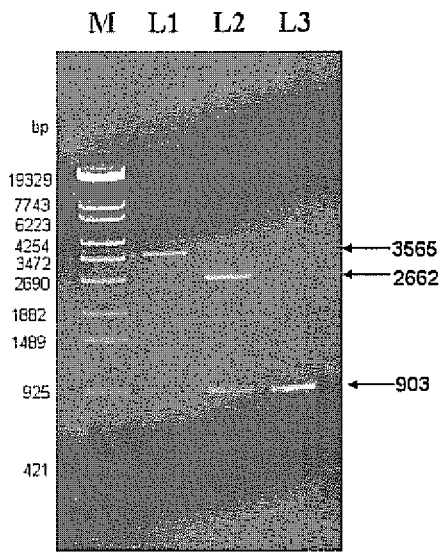
FIG. 3 pUCN vector Restriction Enzyme Digestion Identification and PCR Detection.

Cloning of *Brassica napus* oleosin gene promoter: *Brassica napus* is an important oil crop. The oil content is up to 42~45%. The 20 kD oleosin in *Brassica napus* oil body is 10 times the amount of 24 kD oleosin. Forward primer pBINOA-1: CCC <u>AAGCTT</u> TTC AAC GTG GTC GGA TCA TGA CG (SEQ ID NO:1) and reverse primer pBINOA-2: CGC <u>GGATCC</u> GAA TTG AGA GAG ATC GAA GAG (SEQ ID NO:2) for the PCR amplification of *Brassica napus* 20 kD oleosin gene promoter were designed according to the nucleotide sequence of *Brassica napus* oleosin gene promoter (Genbank No. AF134411) in which HindIII and BamHI cleavage sites were introduced (the underlined section). Using the genome DNA of *Brassica napus* Qingyou 14 variety as the template and pBINOA-1 and pBINOA-2 as primers, *Brassica napus* oleosin gene promoter was amplified by PCR with the following conditions: 94° C. 1 min, 63-73° C. 1 min, and 68° C. 1 min, and 10 min of extension at 68° C. after 30 cycles. The amplification product was recovered by agarose gel electrophoresis, double digested with HindIII and BamHI, and connected to pUC19 digested with HindIII and BamHI. The ligation product was mixed with 2004 of DH5α competent cell (purchased from Tiangen Biotech (Beijing) Co., Ltd.), and then subjected to ice bath for 30 min, heat shock for 1.5 min at 42° C., and ice bath for 3 min. 8004 LB culture medium was added and cultured for 45 min at 37° C. Aliquots of the transformation reaction was plated on LB agar containing 50 µg/mL ampicillin and incubated overnight at 37° C. The transformants were screened by PCR using pBINOA-1 and pBINOA-2 as primers. PCR conditions were 94° C. 1 min, 60-73° C. 1 min, 72° C. 1 min, and 10 min of extension at 72° C. after 30 cycles. The PCR product was subjected to electrophoresis with agarose gel for verification. The positive transformant was named as pUCN. The positive transformant was shaken in liquid culture medium. Plasmid was extracted through alkaline lysis. The plasmid was subjected to single enzyme digestion identification with HindIII and double enzyme digestion identification with HindIII and BamHI. The results displayed by agarose gel electrophoresis are shown in FIG. 3. M: DNA Molecular Weight Marker λDNA/EcoT14I; L1: product of restriction enzyme digestion of pUCN plasmid with HindIII as 3565 bp fragment; L2: products of double digestions of pUCN plasmid with HindIII and BamHI, as the vector fragment of 2662 bp and the promoter of 903 bp; and L3: promoter of 903 bp obtained from PCR detection of pUCN plasmid. pUCN is sequences according to the following procedures: (1) Using pUCN as template, conduct PCR reaction with pUC19 common sequencing primer to obtain PCR product; (2) purify PCR product to remove enzyme, florescent dye, primer, and other ions; (3) use 3730 sequencer (ABI Ltd.) to sequence the purified PCR product after degeneration and ice bath; (4) automatically analyze and print out colored sequencing map and DNA sequence by the machine. The length of the exogenous fragment in pUCN is 903 bp. The sequence is shown in SEQ ID NO:3. The molecular weight is 556.7 kDa. The enzyme digestion results and sequencing results suggest that, *Brassica napus* oleosin gene promoter was successfully cloned into pUC19.

Artificial synthesis of apolipoprotein A-I-$_{Milano}$ gene: Based on apolipoprotein A-I gene sequence (SEQ ID NO:4, NM000039) (amino acid sequence shown in SEQ ID NO:5) and the codon usage of *Helianthus annuus* (http://www.kazusa.or.jp/codon/cgi-bin/showcodon.cgi?species=4232), as well as the GC content in *Helianthus annuus* (genome, apolipoprotein A-I-$_{Milano}$ gene is redesigned and synthesized. Residue C at position 517 was mutated into T, and at the 5' end of the gene a thrombin cleavage site was added, with the nucleotide sequence shown in SEQ ID NO:6 (CTGGTCCCAA GGGGTAGC) and the amino acid sequence shown in SEQ ID NO:7 (L V P R G S). The molecular weight of the synthesized apolipoprotein A-I-$_{Milano}$ gene was 462.4 kDa, and the sequence is shown in SEQ ID NO:8. The encoded protein is composed of 249 amino acid residues and the molecular weight is 28.585 kDa.

Amplification of Ole/apoA-I$_M$ fusion protein gene: Two pairs of specific primers (pBINOA-3/pBINOA-4 and pBINOA-5/pBINOA-6, wherein the sequences are SEQ ID NO:9, SEQ ID NO:10, SEQ ID NO:11, and SEQ ID NO:12 respectively) were designed according to the sequence of *Arachis hypogaea* oleosin gene (Genbank No. AF325917) and the sequence of apolipoprotein A-I-$_{Milano}$ gene (SEQ ID NO:8). pBINOA-3 and pBINOA-6 were provided with BamHI and SacI restriction sites (the underlined section) respectively. Moreover, Kozak sequence (the bolded part in the sequence, to improve the transcription and expression efficiencies) is positioned near the initiator codon of oleosin gene in pBINOA-3 primer. pBINOA-4 and pBINOA-5 were reverse complementary sequences.

```
SEQ ID NO.: 9 pBINOA-3:
CGC GGA TCC AGC AAA GCC GCC ACC ATG GCT ACT

GCT ACT GAT CG

SEQ ID NO.: 10 pBINOA-4:
GCT ACC CCT TGG GAC CAG TGA TGA TGA CCT CTT

AAC

SEQ ID NO.: 11 pBINOA-5:
GTT AAG AGG TCA TCA TCA CTG GTC CCA AGG GGT

AGC

SEQ ID NO.: 12 pBINOA-6:
C GAG CTC TTA TTG TGT GTT AAG TTT CTT TG
```

Figure 4:
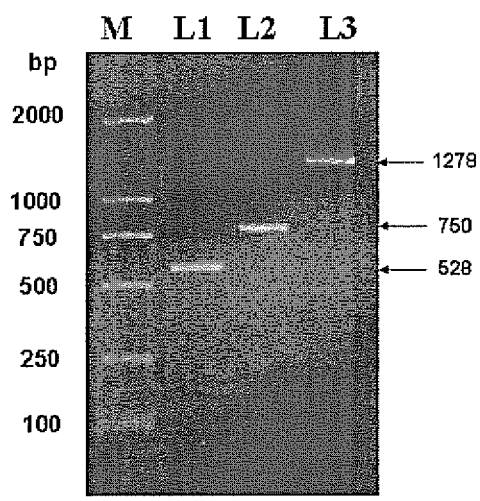
FIG. 4 Construction of Ole/apoA-IM Fusion gene.

Using pBINOA-3/pBINOA-4 as the primer, *Arachis hypogaea* (variety Jihua 4) genome DNA as template, the *Arachis hypogaea* oleosin gene lacking the terminate codon was amplified. PCR conditions are 94° C. 1 min, 50-55° C. 1 min, 68° C. 1 min, and 10 min of extending at 68° C. after 30 cycles. Using pBINOA-5/pBINOA-6 as the primer, the optimized apolipoprotein A-I-$_{Milano}$ as template, the apolipoprotein A-I-$_{Milano}$ gene was amplified. PCR conditions are 94° C. 1 min, 63-73° C. 1 min, 68° C. 1 min, and 10 min of extending at 68° C. after 30 cycles. The two PCR amplification products were recovered by agarose gel electrophoresis, and mixed at the molar ratio of 1:1 to serve as template. pBINOA-3/pBINOA-6 were used as primer for overlapping PCR. PCR conditions are 94° C. 1 min, 50-55° C. 1 min, 68° C. 2 min, and 10 min of extending at 68° C. after 30 cycles. Ole/apoA-I$_M$ fusion gene was obtained through agarose gel electrophoresis of the amplification product. The construction of Ole/apoA-I$_M$ fusion gene is shown in FIG. 4. M: DNA molecular weight marker DL2000; L1: the 528 bp fragment of *Arachis hypogaea* oleosin gene lacking the termination codon, amplified with pBINOA-3/pBINOA-4 as the primer and *Arachis hypogaea* (variety Jihua 4) genome DNA as the template: L2: the 750 bp apolipoprotein A-I-$_{Milano}$ gene amplified with pBINOA-5/pBINOA-6 as the primer and the optimized apolipoprotein A-I-$_{Milano}$ gene as the template (the nucleotide sequence containing thrombin cleavage site); L3: Ole/apoA-I$_M$ fusion gene obtained by overlapping PCR with pBINOA-3/pBINOA-6 as the primer. The Ole/apoA-I$_M$ fusion gene was sequenced, and the results indicated that the sequence of Ole/apoA-I$_M$ fusion gene was as shown in SEQ ID NO:13. The length is 1278 bp, and the molecular weight is 787.9 kDa. The deduced amino acid sequence is shown in SEQ ID NO:14, comprising 425 amino acid residues. The molecular weight is 46.994 kDa. The construction results and sequencing results of oleosin-apoA-I$_M$ fusion gene showed that, we had already obtained ole/apoA-I$_M$ fusion gene.

Figure 5:
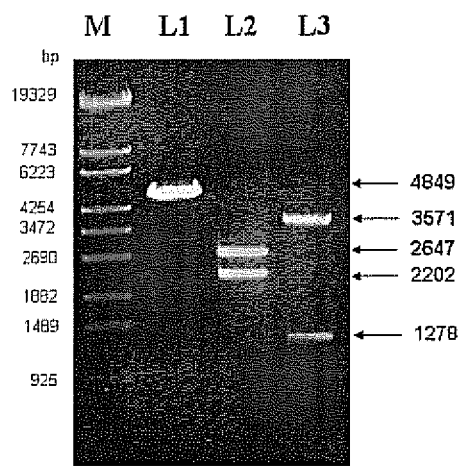
FIG. 5 pUCNOA vector Restriction Enzyme Digestion Identification.

Construction of intermediate vector pUCNOA: The ole/apoA-I$_M$ fusion gene was BamHI and SacI double digested and ligated with pUCN which was double digested in the same way. The ligation product was mixed with 200 μL DH5α competent cell (purchased from Tiangen Biotech (Beijing) Co., Ltd.), and subjected to ice bath for 30 min, heat shock for 1.5 min at 42° C., and ice batch for 3 min. 8004 LB culture medium was added and grown at 37° C. for 45 min. LB agar plate containing 100 μg/mL ampicillin was innoculated and incubated at 37° C. overnight. The transformants were selected by PCR using pBINOA-3 and pBINOA-6 as primers. PCR conditions were 94° C. 1 min, 60-73° C. 1 min, 72° C. 1.5 min, and extension of 10 min at 72° C. after 30 cycles. The PCR product was run on agarose gel. The positive transformant was named as pUCNOA and was shaken in liquid medium. Plasmid was extracted by alkaline lysis. The plasmid was identified by HindIII single digestion identification, HindIII and BamHI double digestion identification, and BamHI and SacI double digestion identification. The identification results of agarose gel electrophoresis are shown in FIG. 5. M: DNA molecular weight marker λDNA/EcoT14I; L1: fragment of 4849 bp obtained by HindIII single digestion of pUCNOA plasmid; L2: vector fragment of 2647 bp and exogenous fragment of 2202 bp (containing *Brassica napus* oleosin gene promoter and ole/apoA-I$_M$ fusion gene) obtained by HindIII and SacI double digestion of pUCNOA plasmid; L3: vector fragment of 3571 bp and exogenous fragment of 1278 bp (ole/apoA-I$_M$ fusion gene) obtained by BamHI and SacI double digestion of pUCNOA plasmid. The pUCNOA plasmid was sequenced, and the sequencing results are shown in SEQ ID NO:15. The total length is 2202 bp and the molecular weight is 1357.5 kDa, including *Brassica napus* oleosin gene promoter and ole/apoA-I$_M$ fusion gene. The enzyme digestion results (as shown in FIG. 5) and sequencing results (as shown in Sequence List) (SEQ ID NO:15) indicated that, the expression cassette of *Brassica napus* oleosin gene promoter-driven *Arachis hypogaea* oleosin gene-apolipoprotein A-I-$_{Milano}$ fusion gene was obtained and the said expression cassette was successfully cloned into the vector pUC19.

Figure 6:
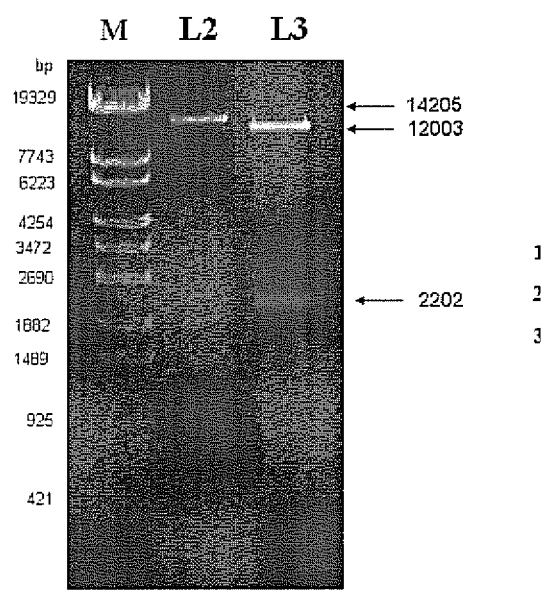
FIG. 6 Restriction Enzyme Digestion Identification of Seed-specific Plant Expression Vector pBINOA.

Construction of seed-specific plant expression vector pBINOA: DNA of pUCNOA plasmid was extracted by alkaline lysis, and cleaved with HindIII and SacI. The exogenous fragment of 2202 bp was recovered by agarose gel electrophoresis and ligated to pBI121 cleaved with HindIII and SacI. The ligation product was mixed with 200 µL DH5α competent cell (purchased from Tiangen Biotech (Beijing) Co., Ltd.), and subjected to ice bath for 30 min, heat shock at 42° C. for 1.5 min, and ice bath for 3 min. 800 µL LB culture medium was added and cultivated for 45 min. LB plate containing 100 µg/mL kanamycin was plated and cultivated at 37° C. overnight. Transformants are screened by PCR using pBINOA-1 and pBINOA-6 as primers. PCR conditions were 94° C. 1 min, 60-73° C. 1 min, 72° C. 2 min, and extension or 10 min at 72° C. after 30 cycles. The PCR product were screened through agarouse gel electrophoresis. The positive transformant was designated as pBINOA. The positive transformant was cultured in liquid while shaking. Plasmid was extracted with alkaline lysis, and subjected to HindIII single digestion identification and HindIII and SacI double digestion. The identification results of agarose gel electrophoresis are shown in FIG. 6. M: DNA molecular weight marker λDNA/EcoT14I; L1: fragment of 14205 bp, the product of HindIII digestion of pBINOA plasmid; L2: vector fragment of 12003 bp and exogenous fragment of 2202 bp (including *Brassica napus* oleosin gene promoter and ole/apoA-$I_M$ fusion gene), the products of HindIII and SacI double digestion of pBINOA plasmid. The pBINOA plasmid was sequenced, and the sequencing result is as shown in SEQ ID NO:15. The full-length nucleotide sequence of the vector is shown as SEQ ID NO:16. The entire expression cassette is 2202 bp long. The molecular weight is 1357.5 kDa, including *Brassica napus* oleosin gene promoter and ole/apoA-$I_M$ fusion gene. *Brassica napus* oleosin gene promoter is a strong seed-specific promoter, and drives the specific expression of apolipoprotein A-I-$_{Milano}$ in oil body as fusion with *Arachis hypogaea* oleosin in the transgenic plant. *Arachis hypogaea* oleosin carrying with apolipoprotein A-I-$_{Milano}$ is anchored on oil body surface. Utilizing the hydrophobic/lipophilic characteristics of oil body, the transgenic plant seeds were ground and extracted, centrifuged, and the upper oil phase recovered, thereby separating the protein from other components in the cell. More than 90% of the seed protein was removed. Thrombin recognition site was positioned between *Arachis hypogaea* oleosin and apolipoprotein A-I-$_{Milano}$ to release apolipoprotein A-I-$_{Milano}$ from oil body.

Example 3: Production of Apolipoprotein A-I-$_{Milano}$ (AIM) with the Vector 3.1 Introduce the Seed-Specific Expression Vector Constructed Above into the Explants of the Receptor Plant;
3.1.1 Preparation of the Competent *Agrobacterium* Cells
(1) Transfer *Agrobacterium tumefacien* LBA4404 single bacterium into 3 mL YEB medium (containing streptomycin Sm 125 µg/mL), and grow the cells at 28° C. overnight;
(2) Transfer 5004 overnight culture into 50 mL YEB (Sm 125 µg/mL) medium, and grow the cells at 28° C. until $OD_{600}$ is 0.5;
(3) 5,000 rpm, centrifuge for 5 min;
(4) Resuspend *Agrobacterium* cells in 10 mL 0.15M NaCl solution, 5,000 rpm, and centrifuge for 5 min;
(5) Resuspend *Agrobacterium* cells in 1 mL precooled 20 mM $CaCl_2$ for ice bath and use within 24 h, or dispense aliquots (200 µl) of the suspensions into tube and quick freeze for 1 min in liquid nitrogen, and preserve at −70° C. for later use.

3.1.2. Transformation of *Agrobacterium* Competent Cells with Seed-Specific Plant Expression Vector
1 µg thus constructed plasmid DNA was added to 2004 competent cells, and stored in liquid nitrogen for 1 min, in water bath at 37° C. for 5 min. Then 1 mL YEB medium was added, cultivated in liquid medium at 28° C. while slowly shaking for 4 h; and centrifuged at 1,000 rpm for 30 sec. The supernatant was discarded and 0.1 mL YEB medium was added for resuspension. Aliquots of the transformation reaction were plated on YEB agar plate containing 100 µg/mL Kan and 124 µg/mL Sm, and incubated at 28° C. for approximately 48 h.
Identification of Positive Clone
Single colony was picked into YEB medium (containing 100 µg/mL Kan and 125 µg/mL Sm), and cultivated in liquid medium at 28° C. overnight. Small amount of plasmid DNA was extracted with alkaline lysis. Using the plasmid DNA as template and pBINOA-1 and pBINOA-6 as primers, PCR amplification identification was carried out under the following conditions: 94° C. 1 min, 60-73° C. 1 min, 72° C. 2 min, and extension of 10 min at 72° C. after 30 cycles. Positive transformants were obtained after agar gel electrophoresis of PCR product.
Preparation of *Agrobacterium* Suspension Used for Oil Sunflower Transformation
5 mL YEB medium containing 100 µg/mL Kan and 125 µg/mL Sm was inoculated with a single colony of transformed *Agrobacterium*. The culture was grown overnight with shaking. 100-200 mL YEB liquid medium containing 100 µg/mL Kan and 125 µg/mL Sm was inoculated with 1 mL culture. The culture was grown at 28° C. with vigorous shaking until $OD_{600}$ is 0.4~0.8, and centrifuged at 3500 rpm for 10 min to recover cells. The pellet was resuspended with MS (free of plant growth regulators or antibiotics) to make $OD_{600}$ at approximately 0.6 for transformation.
3.1.3 Genetic Transformation of Oil Sunflower Explants Mediated by *Agrobacterium*
The explants, in the forms of shoot apexes excised from sterile seedlings, cotyledon, cotyledonary node or seedlings with one cotyledon detached, of the seedling of oil sunflower seeds sprouting for 3~4 d were immersed in said *Agrobacterium* suspension for 6~8 min and transferred to MS solid medium for culture for 3 d (at 25° C., in dark). The seedlings with one cotyledon detached is preferred.
3.2 Cultivation of the Above Receptor Plant Materials into Complete Plant to Obtain Seeds for the Detection of Target Gene and Protein
3.2.1 Cultivate the Receptor Plant Materials into Complete Plant and Obtain Seeds
The transformed explants were transferred to MS agar medium containing 300 mg/L cephalosporin for approximately 7 d, then transferred to MS resistance screening medium (containing 300 mg/L cephalosporin and 70 mg/L kanamycin) for selective culture. The medium was exchanged every 15~20 d. Resistance buds were obtained after three rounds of screening. 2~3 cm resistance buds were transferred to rooting medium MS2 (MS+IBA0.1 mg/L+Kan 70 mg/L+cef 300 mg/L) and transplanted after rootage of resistance seedling into greenhouse for vermiculite and Nutritional soil mixture culture until maturity, seeds harvested.
3.2.2 Target Gene and Protein Detection
PCR detection was performed on apolipoprotein A-I-$_{Milano}$ gene during the Seedling Stage. Western blotting detection was performed on *Arachis hypogaea* oleosin and apolipoprotein A-I-$_{Milano}$ fusion protein after harvesting kernels.

Figure 7:
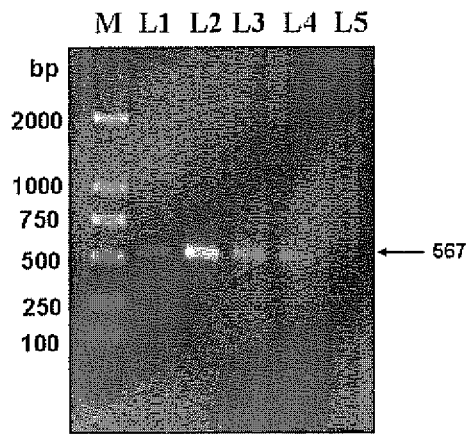
FIG. 7 PCR Detection of npt II Gene in Transgenic Oil Sunflower.
Figure 8:
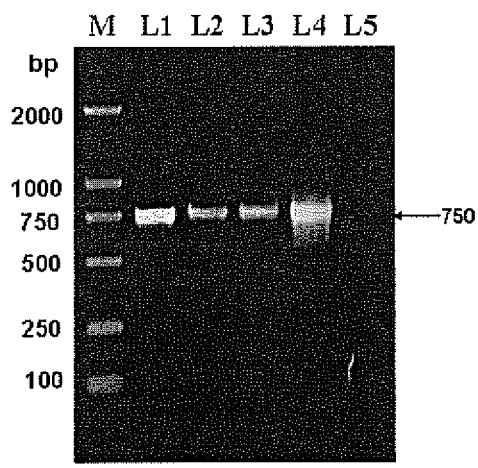
FIG. 8 PCR Detection of apolipoprotein Gene in Transgenic Oil Sunflower.

PCR Detection and PCR-Southern Blotting Detection of Transgenic Oil Sunflower Seedling SDS method was adopted to extract the genome DNA of the young leaves of resistant oil sunflower seedling as the template. PCR amplification was carried out with two pairs of primers nptIIF/nptIIR and pBINOA-5/pBINOA-6. The sequences of the premiers are nptIIF: ATG AAC TGC AGG ACG AGG (SEQ ID NO:17) and GCG ATA CCG TAA AGC ACG (SEQ ID NO:18) respectively. The PCR condition of nptIIF/nptIIR and pBINOA-5/pBINOA-6 includes 94° C. for 1 min, 60° C. for 1 mm, 72° C. for 1 min, and final extension for 10 min at 72° C. after 30 cycles. As anticipated, fragments of 567 bp (partial nptII gene) and apoA-$I_M$ gene fragment of 750 bp were amplified respectively. The results are shown in FIG. 7 and FIG. 8. In FIG. 7, M: DNA molecular weight marker DL2000; L1-L4: the fragment of 567 bp amplified with nptIIF/nptIIR as the primer and the genome DNA extracted from the kanamycin-resistant oil sunflower as the template, i.e., positive plants; L5: use non-resistant oil sunflower as control. In FIG. 8, M: DNA molecular weight marker DL2000; L1-L4: the fragment of 750 bp amplified with pBINOA-5/pBINOA-6 as the primer and the genome DNA extracted from the kanamycin-resistant oil sunflower as the template, i.e., positive plant; L5: use non-resistant oil sunflower as control.

PCR-Southern Blotting Detection

Figure 9:
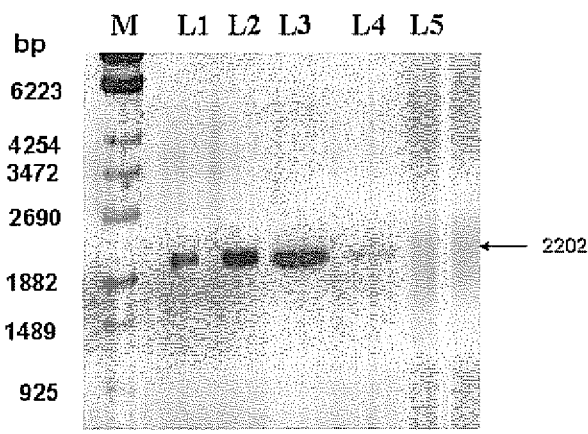
FIG. 9 PCR-Southern Blotting Results of Transgenic Oil Sunflower.

1) Genomic DNA of the young leave of the transgenic oil sunflowers, in which both nptII and apoA-$I_M$ are positive, was extracted with SDS method. PCR amplification was performed on the genome DNA with pBINOA-1/pBINOA-6 as the primer. The PCR reaction condition includes 30 cycles of 94° C. for 1 min, 60° C. for 1 min, and 72° C. for 2.5 min; and final extension at 72° C. for 10 min.
2) The DNA was transferred from agarose gel to a nylon membrane, denatured and neutralized after electrophoresis, and subjected to semi-dry blotting. The membrane was dried and baked for 1.2 hr at 80° C. in a vacuum oven.
3) DNA probe marking The pBINOA plasmid DNA digested with BamH☐ and Sac☐ was recovered. 3 µg DNA was used for labeling.
4) Hybridization The membrane was pre-hybridized at 63° C. for 30 min and hybridized at 63° C. overnight, washed twice with 2×SSC, 0.1% SDS, and then washed twice with 0.5×SSC, 0.1% SDS preheated to 65° C. at 63° C.
5) Detection The hybridized and washed membrane was briefly rinsed once with washing buffer, incubated in 100 ml Blocking solution for 30 min, incubated for 30 min in 20 ml Antibody solution, Washed 2×15 min in 100 ml Washing buffer, and equilibrated for 2-5 min in 20 ml Detection buffer. The membrane was placed in a hybridization bag (with DNA side facing up) and 1 ml CSPD added. The membrane was incubated for 10 min at 37° C. to enhance the luminescent reaction, and exposed to X-ray film at room temperature. The results are shown in FIG. 9. M: DNA molecular weight marker λ DNA/EcoT14I; L1-L4: the Southern blotting results of the product amplified with the positive plant genome (detected as positive by PCR) as the template and pBINOA-1/pBINOA-6 as the primer. The hybridization signal was displayed at the place of 2.2 kb as expected, suggesting the integration of ole/-apoA-$I_M$ fusion gene into oil sunflower genome; L5: control of non-transgenic oil sunflower.

Figure 10:
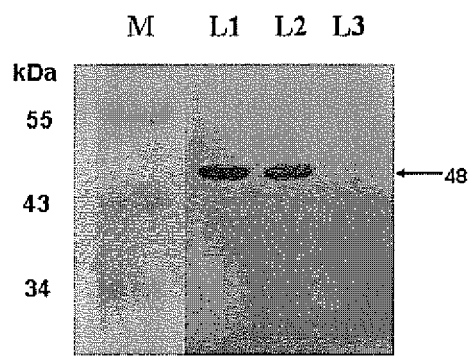
FIG. 10 Western Detection of the oleosin-Apolipoprotein A-I-$_{Milano}$ Fusion Protein in Transgenic Oil Sunflower Kernel Oil Body.

Western Blotting Detection of *Arachis hypogaea* Oleosin and Apolipoprotein A-I-$_{Milano}$ Fusion Protein in Transgenic Oil Sunflower Seeds Transgenic oil sunflower seeds were ground in five volumes of grinding buffer (50 mM Tris-HCl pH 7.5, 0.4 M sucrose, 0.5M NaCl), centrifugated 10×g for 30 min, and separated into three parts. The oil phase was collected and resuspend in one volume of grinding buffer and mixed even. Five volumes of precooled 50 mM Tris-HCl pH 7.5 buffer was added, centrifugated 10×g for 30 min, and the oil phase collected. The above processes were repeated for two times to further remove the remaining water-soluble ingredients and insoluble ingredients, obtaining pure oil body (the ingredients of oil body include: neutral lipids, phosphatides, and oleosin). To the oil body was added 2V of diethyl ether and centrifugated. The neutral lipids were in the upper diethyl ether layer and phosphatides were left in the lower water phase. The intermediate protein layer was collected and suspended in 0.1M sucrose buffer. Chloroform methanol (2:1) mixture was added and extracted twice. The intermediate protein layer was collected, extracted with diethyl ether once and dissolved in sterile water. SDS polyacrylamide gel electrophoresis was performed, and then Western blotting analysis was performed using polyclonal goat anti-rabbit apolipoprotein A-I after transmembrane. The results are shown in FIG. 10. M: protein molecular weight standard; L1 and L2: oil protein extracted from transgenic oil sunflower seeds, expression of apolipoprotein A-I-$_{Milano}$ is shown. A fusion protein of molecular mass of approximately 48 kDa was recognized, consistent with the anticipated result (*Arachis hypogaea* oleosin 18.4 kDa, thrombin cleavage site 0.6 kDa, and apolipoprotein A-I-$_{Milano}$ 28.9 kDa). The fusion protein accounts for 1.1% of the total seed protein, exceeding the minimum commercialization requirement (1%) of recombinant medical protein in plant. Therefore, it is feasible and applicable to make use of plant oil body expression system to achieve the industrial production of apolipoprotein A-I-$_{Milano}$.

3.3 Obtain Apolipoprotein A-I-$_{Milano}$ from the Seeds by Separation and Purification.

Step 1: Separate Oil Body from Other Components in Seeds

The kernel was ground in five volumes of grinding buffer (50 mM Tris-HCl pH 7.5, 0.4M sucrose, 0.5 M NaCl), centrifuged at 10×g for 30 min, and divided into three parts. The bottom part is insoluble precipitation (hull, fiber materials, insoluble sugar, protein and other insoluble dirt); the middle layer is aqueous phase, containing soluble cellular constituents (storage protein); the upper layer is the oil body and the associated oil body protein.

Step 2: Wash the Oil Body

The oil phase obtained from Step 1 was resuspended in the same volume of grinding butter and mixed even. Five volumes of precooled 50 m MTris-HCl pH 7.5 buffer are added and centrifuged at 10×g for 30 min. The oil phase was collected. The above processes were repeated twice to further remove the residual water-soluble ingredients and insoluble ingredients. The washed oil body was resuspended in precooled 50 mM Tris-HCl pH 7.5 of equivalent volume. The resulting oil body was substantially pure oil body, and he only protein left was oil body protein.

Step 3: Release Apolipoprotein A-I-$_{Milano}$ Protein by Restrictive Digestion

The oil body was washed with thrombin digestion buffer (20 m M Tris-HCl pH8.4, 150 m M NaCl, and 2.5 m M $CaCl_2$) for two times. Appropriate amount of thrombin was added, stored at 37° C. overnight, and centrifuged. Apolipoprotein protein exists in the aqueous phase.

Step 4: Purify Apolipoprotein A-I-$_{Milano}$ Protein with High Performance Liquid Chromatography (HPLC)

Reversed-phase chromatography C4 column (5μ, 0.24*25 cm) was used, at the ultraviolet wavelength of 214 nm. The column was equilibrated with 2 mL/min buffer A (10% acetonitrile, 0.1% trifluoroacetic acid), loaded with the aqueous phase obtained in the last step, and applied linear gradient elution of 0-60% buffer B (95% acetonitrile, 0.1% trifluoroacetic acid). Pure apolipoprotein A-I-$_{Milano}$ protein was obtained with the purity above 99.5%.

Example 4: Comparison Between Oil Sunflower and Carthamus Tinctorius as Bioreactor for the Production of Apolipoprotein A-I-$_{Milano}$ (AIM)

Figure 11:
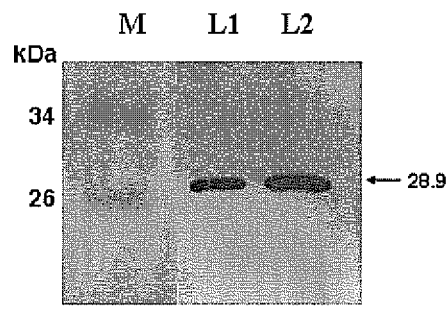
FIG. 11 Western Detection of the trans-apolipoprotein A-I-$_{Milano}$ gene oil sunflower seed and *carthamus tinctorius* seed to obtain apolipoprotein A-I-$_{Milano}$ protein by separation and purification.

The same amount (280 mg) of trans-apolipoprotein A-I-$_{Milano}$ gene oil sunflower seed and carthamus tinctorius seed were used to obtain apolipoprotein A-I-$_{Milano}$ protein by separation and purification according to Example 3. The loading quantity was one-tenth of the total quantity obtained. Western blotting detection was performed, and the results are shown in FIG. 11. M: protein molecular weight standard; L1: apolipoprotein A-I-$_{Milano}$ purified from transgenic carthamus 28.9 kDa as expected, with the amount of 50 ng; L2: the apolipoprotein A-I-$_{Milano}$ purified from transgenic oil sunflower, 28.9 kDa as expected, with the amount of 80 ng. It can be calculated that 1 kg of transgenic oil sunflower seed can produce 2.85 g of apolipoprotein A-I-$_{Milano}$, while under the same condition, 1 kg transgenic carthamus tinctorius seed can produce 1.78 g of apolipoprotein A-I-$_{Milano}$. Moreover, the yield per mu of oil sunflower is approximately 250 kg while that of carthamus tinctorius is approximately 200 kg. Therefore, oil sunflower is superior to carthamus tinctorius in terms of the yield of apolipoprotein A-I-$_{Milano}$ protein per seed weight or per plant area.

---

The invention claimed is:

1. An expression vector comprising a *Brassica napus* oleosin gene promoter operably linked to a DNA sequence encoding:

an apolipoprotein A-I$_{Milano}$ fused with an *Arachis hypogaea* oleosin, wherein the vector comprises the sequence as shown in SEQ ID NO: 15.

2. A method for the construction of the expression vector as described in claim 1, including the following procedures:
1) isolate and clone the *Brassica napus* oleosin promoter and the *Arachis hypogaea* oleosin gene;
2) design and synthesis the apolipoprotein A-I$_{Milano}$ gene according to *Helianthus annuus* codon usage; and
3) construct the expression vector in which the nucleic acid encoding the fusion protein of *Arachis hypogaea* oleosin with apolipoprotein A-I$_{Milano}$ is driven by the *Brassica napus* oleosin gene promoter;

wherein the expression vector comprises SEQ ID NO: 15.

3. A method according to claim 1, wherein in step (3), *Arachis hypogaea* oleosin gene and apolipoprotein A-I$_{Milano}$ gene are constructed as a fusion gene by overlapping PCR.

4. A method for producing apolipoprotein A-I$_{Milano}$, including the following steps:
1) introducing the expression vector as claimed in claim 1 into an explant of an oil sunflower;
2) cultivating the oil sunflower material into a mature plant, the plant including seeds, and
3) collecting the seeds thereof; and;
4) purifying apolipoprotein A-I$_{Milano}$ from the seeds.

5. The method according to claim 4, wherein the introduction method in Step 1) is *Agrobacterium*-mediated transformation.

6. The method according to claim 4, wherein the oil sunflower seed has a kanamycin resistance phenotype.

7. The method according to claim 4, wherein the purification method is high-performance liquid chromatography (HPLC).

8. The method according to claim 4, wherein the purification includes grinding the seed containing apolipoprotein A-I$_{Milano}$ in a buffer solution, separating an oil body from other components by centrifugation, washing the oil body, releasing the apolipoprotein A-I$_{Milano}$ from the surface of the oil body through digestion, and obtaining apolipoprotein A-I$_{Milano}$ through HPLC purification.

* * * * *

SEQUENCE LISTING

```
<160> NUMBER OF SEQ ID NOS: 18

<210> SEQ ID NO 1
<211> LENGTH: 32
<212> TYPE: DNA
<213> ORGANISM: Brassica Campestris

<400> SEQUENCE: 1
cccaagcttt tcaacgtggt cggatcatga cg                                   32

<210> SEQ ID NO 2
<211> LENGTH: 30
<212> TYPE: DNA
<213> ORGANISM: Brassica Campestris

<400> SEQUENCE: 2
cgcggatccg aattgagaga gatcgaagag                                      30

<210> SEQ ID NO 3
<211> LENGTH: 903
<212> TYPE: DNA
<213> ORGANISM: Brassica Campestris

<400> SEQUENCE: 3
ttcaacgtgg tcagatcatg acgcttccag aaaacatcga gcaagctctc aaagctgatc    60
tctttcggat cgtactgaac ccgaacaatc tcgttatgcc ccgtcgtctc cgaacagaca   120
tcctcgtagc tcggattgtc gacgaatcca tggctatacc caacctccgt cttcgtcacg   180
ccaggaaccc tctggtaagc cagttccgct ccccagaaac aaccggcgcc gaattgcgcg   240
aattgctgac ctggagacgg aacatcgtca tcgggtcctt gcgcgattgc ggcggaagcc   300
gggtcgggtt ggggacgaga cccgaatccg agcctggtga agaggttgtt catcggagat   360
ttgtagactg agatggatcg agcggttttg gggaaagggg aagtgggttt ggtttttttg   420
gatagagaga gtgcagcttt ggagagagac tggagaggtt tagagagaga cgcggcggag   480
attaccggag gagaggcgac gagagatagc attatcgaaa ggaagggaga aagagtgacg   540
tggagaaata agaaacccgt taagagtctg atatttatta tattaaaagc ccaatgggcc   600
taaacccatt taaacaagac agataaatgg gccgtgtgtt aagttaacag agtgttaacg   660
ttcggtttca aatgccaacg ccataggaac aaaacaaacg tgtcctcaag taaacccctg   720
```

-continued

```
ccgtttacac ctcaatggct gcatggtgaa gccattaaca cgtggcgtag gatgcatgac      780
gacgccattg acacctgact ctcttcccct ctcttcatat atctctaatc aattcaacta      840
ctcattgtca tagctattcg gaaaatacat acacatcctt ttctcttcga tctctctcaa      900
ttc                                                                    903
```

<210> SEQ ID NO 4
<211> LENGTH: 732
<212> TYPE: DNA
<213> ORGANISM: Homo Sapiens

<400> SEQUENCE: 4

```
gatgaacccc cccagagccc ctgggatcga gtgaaggacc tggccactgt gtacgtggat       60
gtgctcaaag acagcggcag agactatgtg tcccagtttg aaggctccgc cttgggaaaa      120
cagctaaacc taaagctcct tgacaactgg acagcgtga cctccacctt cagcaagctg       180
cgcgaacagc tcggccctgt gacccaggag ttctggggata acctggaaaa ggagacagag      240
ggcctgaggc aggagatgag caaggatctg gaggaggtga aggccaaggt gcagccctac      300
ctggacgact tccagaagaa gtggcaggag gagatggagc tctaccgcca gaaggtggag      360
ccgctgcgcg cagagctcca gagggcgcg cgccagaagc tgcacgagct gcaagagaag       420
ctgagcccac tgggcgagga gatgcgcgac cgcgcgcgcg cccatgtgga cgcgctgcgc      480
acgcatctgg ccccctacag cgacgagctg cgccagcgct tggccgcgcg ccttgaggct      540
ctcaaggaga acggcggcgc cagactggcc gagtaccacg ccaaggccac cgagcatctg      600
agcacgctca gcgagaaggc caagcccgcg ctcgaggacc tccgccaagg cctgctgccc      660
gtgctggaga gcttcaaggt cagcttcctg agcgctctcg aggagtacac taagaagctc      720
aacacccagt ga                                                         732
```

<210> SEQ ID NO 5
<211> LENGTH: 243
<212> TYPE: PRT
<213> ORGANISM: Homo Sapiens

<400> SEQUENCE: 5

```
Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Arg Glu Gln Leu
    50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
    130                 135                 140

Gly Glu Glu Met Arg Asp Arg Ala Arg Ala His Val Asp Ala Leu Arg
145                 150                 155                 160
```

```
Thr His Leu Ala Pro Tyr Ser Asp Glu Leu Arg Gln Arg Leu Ala Ala
            165                 170                 175

Arg Leu Glu Ala Leu Lys Glu Asn Gly Gly Ala Arg Leu Ala Glu Tyr
        180                 185                 190

His Ala Lys Ala Thr Glu His Leu Ser Thr Leu Ser Glu Lys Ala Lys
    195                 200                 205

Pro Ala Leu Glu Asp Leu Arg Gln Gly Leu Leu Pro Val Leu Glu Ser
210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 6
<211> LENGTH: 18
<212> TYPE: DNA
<213> ORGANISM: Artificial Sequence
<220> FEATURE:
<223> OTHER INFORMATION: Completely Synthesized

<400> SEQUENCE: 6
ctggtcccaa ggggtagc                                                   18

<210> SEQ ID NO 7
<211> LENGTH: 6
<212> TYPE: PRT
<213> ORGANISM: Artificial Sequence
<220> FEATURE:
<223> OTHER INFORMATION: Completely Synthesized

<400> SEQUENCE: 7

Leu Val Pro Arg Gly Ser
1               5

<210> SEQ ID NO 8
<211> LENGTH: 750
<212> TYPE: DNA
<213> ORGANISM: Artificial Sequence
<220> FEATURE:
<223> OTHER INFORMATION: Completely Synthesized

<400> SEQUENCE: 8
ctggtcccaa ggggtagcga tgaaccaccg cagtctccat gggatagggt gaaagatctg     60
gcgactgtgt atgttgacgt gttgaaggat tctggcagag attacgtctc tcagtttgaa    120
ggttccgcac tcgggaagca actaaatctt aaacttttgg ataactggga cagtgtaaca    180
agtacgttct cgaagctgcg agaacagctc ggcccggtga cccaagaatt ctgggataac    240
cttgaaaaag aaaccgaggg tctcaggcaa gagatgtcca aggacttaga ggaggttaaa    300
gctaaagttc agccttattt ggatgacttt cagaaaaagt ggcaggagga aatggagttg    360
taccgccaaa aagttgaacc ccttagagct gagttgcaag agggtgcacg ccagaagtta    420
cacgagttac aagaaaagct ctcacctttg ggagaggaga tgagagacag ggcgcgtgcg    480
catgtagatg ccttgcgtac tcatcttgct ccatattctg atgaattgag acaatgtctt    540
gctgcacgtc tggaagcctt aaaggaaaat ggggagcac ggctagctga gtatcatgct    600
aaagcaaccg agcaccttag cactcttttcg gaaaaggcca aacccgcttt agaagatcta    660
cgacaaggac tcctacctgt tttggaatca tttaaggtta gtttcctctc agcccttgaa    720
gaatacacaa agaaacttaa cacacaataa                                     750
```

<210> SEQ ID NO 9
<211> LENGTH: 44
<212> TYPE: DNA
<213> ORGANISM: Artificial Sequence
<220> FEATURE:
<223> OTHER INFORMATION: Completely Synthesized

<400> SEQUENCE: 9
cgcggatcca gcaaagccgc caccatggct actgctactg atcg        44

<210> SEQ ID NO 10
<211> LENGTH: 36
<212> TYPE: DNA
<213> ORGANISM: Artificial Sequence
<220> FEATURE:
<223> OTHER INFORMATION: Completely Synthesized

<400> SEQUENCE: 10
gctacccctt gggaccagtg atgatgacct cttaac        36

<210> SEQ ID NO 11
<211> LENGTH: 36
<212> TYPE: DNA
<213> ORGANISM: Artificial Sequence
<220> FEATURE:
<223> OTHER INFORMATION: Completely Synthesized

<400> SEQUENCE: 11
gttaagaggt catcatcact ggtcccaagg ggtagc        36

<210> SEQ ID NO 12
<211> LENGTH: 30
<212> TYPE: DNA
<213> ORGANISM: Artificial Sequence
<220> FEATURE:
<223> OTHER INFORMATION: Completely Synthesized

<400> SEQUENCE: 12
cgagctctta ttgtgtgtta agtttctttg        30

<210> SEQ ID NO 13
<211> LENGTH: 1278
<212> TYPE: DNA
<213> ORGANISM: Artificial Sequence
<220> FEATURE:
<223> OTHER INFORMATION: Completely Synthesized

<400> SEQUENCE: 13
atggctactg ctactgatcg tgcacctcac caggttcaag ttcacacccc caccacacaa        60
cgcgtcgacg ttccacgccg cggctacgat gttagtggtg gtggtattaa gactcttctc       120
cccgagagag gtccgtccac ctctcaaatc atcgccgtcc tcgtcggcgt ccccactggg       180
ggcactctgt tgctcctctc cggcctttca cttctcggaa ccataatcgg gctggcaatt       240 gccacccccgg ttttatctt cttcagcccg gttatagttc ccgcggtcgt taccattgga       300
cttgcagtca ctggtattct cacggcggga gcatgtggac taaccgggct gatgtctttg       360
tcatggatga ttaacttcat ccgacaggta catgggacga cggtgccgga tcagctggac       420
tcagtgaagc ggcgcatggc ggacatggcg gattacgtgg ggcagaagac aaaggatgct       480
ggccaagaga tacagactaa ggcccaggat gttaagaggt catcatcact ggtcccaagg       540
ggtagcgatg aaccaccgca gtctccatgg gatagggtga agatctggc gactgtgtat       600 gttgacgtgt tgaaggattc tggcagagat tacgtctctc agtttgaagg ttccgcactc       660

-continued

```
gggaagcaac taaatcttaa acttttggat aactgggaca gtgtaacaag tacgttctcg      720
aagctgcgag aacagctcgg cccggtgacc caagaattct gggataacct tgaaaaagaa      780
accgagggtc tcaggcaaga gatgtccaag gacttagagg aggttaaagc taaagttcag      840
ccttatttgg atgactttca gaaaaagtgg caggaggaaa tggagttgta ccgccaaaaa      900
gttgaacccc ttagagctga gttgcaagag ggtgcacgcc agaagttaca cgagttacaa      960
gaaaagctct cacctttggg agaggagatg agagacaggg cgcgtgcgca tgtagatgcc     1020
ttgcgtactc atcttgctcc atattctgat gaattgagac aatgtcttgc tgcacgtctg     1080
gaagccttaa aggaaaatgg gggagcacgg ctagctgagt atcatgctaa agcaaccgag     1140
caccttagca ctctttcgga aaaggccaaa cccgctttag aagatctacg acaaggactc     1200
ctacctgttt tggaatcatt taaggttagt ttcctctcag cccttgaaga atacacaaag     1260
aaacttaaca cacaataa                                                   1278
```

<210> SEQ ID NO 14
<211> LENGTH: 425
<212> TYPE: PRT
<213> ORGANISM: Artificial Sequence
<220> FEATURE:
<223> OTHER INFORMATION: Completely Synthesized

<400> SEQUENCE: 14

```
Met Ala Thr Ala Thr Asp Arg Ala Pro His Gln Val Gln Val His Thr
1               5                   10                  15

Pro Thr Thr Gln Arg Val Asp Val Pro Arg Arg Gly Tyr Asp Val Ser
            20                  25                  30

Gly Gly Gly Ile Lys Thr Leu Leu Pro Glu Arg Gly Pro Ser Thr Ser
        35                  40                  45

Gln Ile Ile Ala Val Leu Val Gly Val Pro Thr Gly Gly Thr Leu Leu
    50                  55                  60

Leu Leu Ser Gly Leu Ser Leu Leu Gly Thr Ile Ile Gly Leu Ala Ile
65                  70                  75                  80

Ala Thr Pro Val Phe Ile Phe Phe Ser Pro Val Ile Val Pro Ala Val
                85                  90                  95

Val Thr Ile Gly Leu Ala Val Thr Gly Ile Leu Thr Ala Gly Ala Cys
            100                 105                 110

Gly Leu Thr Gly Leu Met Ser Leu Ser Trp Met Ile Asn Phe Ile Arg
        115                 120                 125

Gln Val His Gly Thr Thr Val Pro Asp Gln Leu Asp Ser Val Lys Arg
    130                 135                 140

Arg Met Ala Asp Met Ala Asp Tyr Val Gly Gln Lys Thr Lys Asp Ala
145                 150                 155                 160

Gly Gln Glu Ile Gln Thr Lys Ala Gln Asp Val Lys Arg Ser Ser Ser
                165                 170                 175

Leu Val Pro Arg Gly Ser Asp Glu Pro Pro Gln Ser Pro Trp Asp Arg
            180                 185                 190

Val Lys Asp Leu Ala Thr Val Tyr Val Asp Val Leu Lys Asp Ser Gly
        195                 200                 205

Arg Asp Tyr Val Ser Gln Phe Glu Gly Ser Ala Leu Gly Lys Gln Leu
    210                 215                 220

Asn Leu Lys Leu Leu Asp Asn Trp Asp Ser Val Thr Ser Thr Phe Ser
225                 230                 235                 240

Lys Leu Arg Glu Gln Leu Gly Pro Val Thr Gln Glu Phe Trp Asp Asn
```

```
                        245                 250                 255
Leu Glu Lys Glu Thr Glu Gly Leu Arg Gln Glu Met Ser Lys Asp Leu
            260                 265                 270

Glu Glu Val Lys Ala Lys Val Gln Pro Tyr Leu Asp Asp Phe Gln Lys
        275                 280                 285

Lys Trp Gln Glu Met Glu Leu Tyr Arg Gln Lys Val Glu Pro Leu
    290                 295                 300

Arg Ala Glu Leu Gln Gly Ala Arg Gln Lys Leu His Glu Leu Gln
305                 310                 315                 320

Glu Lys Leu Ser Pro Leu Gly Glu Glu Met Arg Asp Arg Ala Arg Ala
            325                 330                 335

His Val Asp Ala Leu Arg Thr His Leu Ala Pro Tyr Ser Asp Glu Leu
            340                 345                 350

Arg Gln Cys Leu Ala Ala Arg Leu Glu Ala Leu Lys Glu Asn Gly Gly
            355                 360                 365

Ala Arg Leu Ala Glu Tyr His Ala Lys Ala Thr Glu His Leu Ser Thr
370                 375                 380

Leu Ser Glu Lys Ala Lys Pro Ala Leu Glu Asp Leu Arg Gln Gly Leu
385                 390                 395                 400

Leu Pro Val Leu Glu Ser Phe Lys Val Ser Phe Leu Ser Ala Leu Glu
            405                 410                 415

Glu Tyr Thr Lys Lys Leu Asn Thr Gln
            420                 425

<210> SEQ ID NO 15
<211> LENGTH: 2202
<212> TYPE: DNA
<213> ORGANISM: Artificial Sequence
<220> FEATURE:
<223> OTHER INFORMATION: Completely Synthesized

<400> SEQUENCE: 15
ttcaacgtgg tcagatcatg acgcttccag aaaacatcga gcaagctctc aaagctgatc      60
tctttcggat cgtactgaac ccgaacaatc tcgttatgcc ccgtcgtctc cgaacagaca     120
tcctcgtagc tcggattgtc gacgaatcca tggctatacc caacctccgt cttcgtcacg     180
ccaggaaccc tctggtaagc cagttccgct ccccagaaac aaccggcgcc gaattgcgcg     240
aattgctgac ctggagacgg aacatcgtca tcgggtcctt gcgcgattgc ggcggaagcc     300
gggtcgggtt ggggacgaga cccgaatccg agcctggtga agaggttgtt catcggagat     360
ttgtagactg agatggatcg agcggttttg gggaaagggg aagtgggttt ggttttttg     420 gatagagaga gtgcagcttt ggagagagac tgagaggtt tagagagaga gcggcggag     480 attaccggag gagaggcgac gagagatagc attatcgaaa ggaagggaga aagagtgacg     540
tggagaaata agaaacccgt taagagtctg atatttatta tattaaaagc ccaatgggcc     600
taaacccatt taaacaagac agataaatgg gccgtgtgtt aagttaacag agtgttaacg     660
ttcggtttca aatgccaacg ccataggaac aaaacaaacg tgtcctcaag taaaccctg     720 ccgtttacac ctcaatggct gcatggtgaa gccattaaca cgtggcgtag gatgcatgac     780
gacgccattg acacctgact ctcttcctt ctcttcatat atctctaatc aattcaacta     840
ctcattgtca tagctattcg gaaaatacat acacatcctt ttctcttcga tctctctcaa     900
ttcggatcca gcaaagccgc caccatggct actgctactg atcgtgcacc tcaccaggtt     960
caagttcaca cccccaccac acaacgcgtc gacgttccac gccgcggcta cgatgttagt    1020
```

```
ggtggtggta ttaagactct tctccccgag agaggtccgt ccacctctca aatcatcgcc    1080
gtcctcgtcg gcgtcccccac tgggggcact ctgttgctcc tctccggcct ttcacttctc    1140
ggaaccataa tcgggctggc aattgccacc ccggtttta tcttcttcag cccggttata    1200
gttcccgcgg tcgttaccat tggacttgca gtcactggta ttctcacggc gggagcatgt    1260
ggactaaccg ggctgatgtc tttgtcatgg atgattaact tcatccgaca ggtacatggg    1320
acgacggtgc cggatcagct ggactcagtg aagcggcgca tggcggacat gcggattac     1380 gtggggcaga agacaaagga tgctggccaa gagatacaga ctaaggccca ggatgttaag    1440
aggtcatcat cactggtccc aagggggtagc gatgaaccac cgcagtctcc atgggatagg    1500
gtgaaagatc tggcgactgt gtatgttgac gtgttgaagg attctggcag agattacgtc    1560
tctcagtttg aaggttccgc actcgggaag caactaaatc ttaaacttttt ggataactgg    1620 gacagtgtaa caagtacgtt ctcgaagctg cgagaacagc tcggcccggt gacccaagaa    1680
ttctgggata accttgaaaa agaaaccgag ggtctcaggc aagagatgtc caaggactta    1740
gaggaggtta aagctaaagt tcagcctat ttggatgact ttcagaaaaa gtggcaggag     1800
gaaatggagt tgtaccgcca aaagttgaa ccccttagag ctgagttgca gagggtgca     1860 cgccagaagt tacacgagtt acaagaaaag ctctcacctt tgggagagga gatgagagac    1920
agggcgcgtg cgcatgtaga tgccttgcgt actcatcttg ctccatattc tgatgaattg    1980
agacaatgtc ttgctgcacg tctggaagcc ttaaaggaaa atgggggagc acggctagct    2040
gagtatcatg ctaaagcaac cgagcacctt agcactcttt cggaaaaggc caaacccgct    2100
ttagaagatc tacgacaagg actcctacct gtttttggaat catttaaggt tagtttcctc    2160
tcagcccttg aagaatacac aaagaaactt aacacacaat aa                       2202

<210> SEQ ID NO 16
<211> LENGTH: 14205
<212> TYPE: DNA
<213> ORGANISM: Artificial Sequence
<220> FEATURE:
<223> OTHER INFORMATION: Completely Synthesized

<400> SEQUENCE: 16
tgagcgtcgc aaaggcgctc ggtcttgcct tgctcgtcgg tgatgtactt caccagctcc      60
gcgaagtcgc tcttcttgat ggagcgcatg gggacgtgct tggcaatcac gcgcaccccc     120
cggccgtttt agcggctaaa aaagtcatgg ctctgccctc gggcggacca cgcccatcat     180
gaccttgcca agtcgtcct gcttctcttc gatcttcgcc agcagggcga ggatcgtggc      240
atcaccgaac cgcgccgtgc gcgggtcgtc ggtgagccag agtttcagca ggccgcccag     300
gcggcccagg tcgccattga tgcgggccag ctcgcggacg tgctcatagt ccacgacgcc     360
cgtgattttg tagccctggc cgacggccag caggtaggcc gacaggctca tgccggccgc     420
cgccgccttt tcctcaatcg ctcttcgttc gtctggaagg cagtacacct tgataggtgg     480
gctgcccttc ctggttggct tggtttcatc agccatccgc ttgccctcat ctgttacgcc     540
ggcggtagcc ggccagcctc gcagagcagg attcccgttg agcaccgcca ggtgcgaata     600
agggacagtg aagaaggaac acccgctcgc gggtgggcct acttcaccta tcctgcccgg     660
ctgacgccgt tggatacacc aaggaaagtc tacacgaacc ctttggcaaa atcctgtata     720
tcgtgcgaaa aaggatggat ataccgaaaa atcgctata atgaccccga agcagggtta     780
tgcagcggaa aagcgccacg cttcccgaag ggagaaaggc ggacaggtat ccggtaagcg     840
gcagggtcgg aacaggagag cgcacgaggg agcttccagg gggaaacgcc tggtatcttt     900
```

```
atagtcctgt cgggtttcgc cacctctgac ttgagcgtcg atttttgtga tgctcgtcag      960
gggggcggag cctatggaaa aacgccagca acgcggcctt tttacggttc ctggccttttt   1020 gctggccttt tgctcacatg ttctttcctg cgttatcccc tgattctgtg gataaccgta    1080
ttaccgcctt tgagtgagct gataccgctc gccgcagccg aacgaccgag cgcagcgagt    1140
cagtgagcga ggaagcggaa gagcgccaga aggccgccag agaggccgag cgcggccgtg    1200
aggcttggac gctagggcag ggcatgaaaa agcccgtagc gggctgctac gggcgtctga    1260
cgcggtggaa aggggagggg atgttgtct acatggctct gctgtagtga gtgggttgcg     1320
ctccggcagc ggtcctgatc aatcgtcacc ctttctcggt ccttcaacgt tcctgacaac    1380
gagcctcctt ttcgccaatc catcgacaat caccgcgagt ccctgctcga acgctgcgtc    1440
cggaccggct tcgtcgaagg cgtctatcgc ggcccgcaac agcggcgaga gcggagcctg    1500
ttcaacggtg ccgccgcgct cgccggcatc gctgtcgccg gcctgctcct caagcacggc    1560
cccaacagtg aagtagctga ttgtcatcag cgcattgacg gcgtccccgg ccgaaaaacc    1620
cgcctcgcag aggaagcgaa gctgcgcgtc ggccgttttcc atctgcggtg cgcccggtcg   1680
cgtgccggca tggatgcgcg cgccatcgcg gtaggcgagc agcgcctgcc tgaagctgcg    1740
ggcattcccg atcagaaatg agcgccagtc gtcgtcggct ctcggcaccg aatgcgtatg    1800
attctccgcc agcatggctt cggccagtgc gtcgagcagc gcccgcttgt tcctgaagtg    1860
ccagtaaagc gccggctgct gaaccccccaa ccgttccgcc agtttgcgtg tcgtcagacc   1920
gtctacgccg acctcgttca acaggtccag ggcggcacgg atcactgtat tcggctgcaa    1980 cttttgtcatg cttgacactt tatcactgat aaacataata tgtccaccaa cttatcagtg   2040
ataaagaatc cgcgcgttca atcggaccag cggaggctgg tccggaggcc agacgtgaaa    2100
cccaacatac ccctgatcgt aattctgagc actgtcgcgc tcgacgctgt cggcatcggc    2160
ctgattatgc cggtgctgcc gggcctcctg cgcgatctgg ttcactcgaa cgacgtcacc    2220
gcccactatg gcattctgct ggcgctgtat gcgttggtgc aatttgcctg cgcacctgtg    2280
ctgggcgcgc tgtcggatcg tttcgggcgg cggccaatct tgctcgtctc gctggccggc    2340
gccagatctg gggaaccctg tggttggcat gcacatacaa atggacgaac ggataaacct    2400
tttcacgccc ttttaaatat ccgattattc taataaacgc tcttttctct taggtttacc    2460
cgccaatata tcctgtcaaa cactgatagt ttaaactgaa ggcgggaaac gacaatctga    2520
tcatgagcgg agaattaagg gagtcacgtt atgaccccccg ccgatgacgc gggacaagcc   2580
gttttacgtt tggaactgac agaaccgcaa cgttgaagga gccactcagc cgcgggtttc    2640
tggagtttaa tgagctaagc acatacgtca gaaaccatta ttgcgcgttc aaaagtcgcc    2700
taaggtcact atcagctagc aaatatttct tgtcaaaaat gctccactga cgttccataa    2760
attcccctcg gtatccaatt agagtctcat attcactctc aatccaaata atctgcaccg    2820
gatctggatc gtttcgcatg attgaacaag atggattgca cgcaggttct ccggccgctt    2880
gggtggagag gctattcggc tatgactggg cacaacagac aatcggctgc tctgatgccg    2940
ccgtgttccg gctgtcagcg cagggggcgcc cggttctttt tgtcaagacc gacctgtccg   3000
gtgccctgaa tgaactgcag gacgaggcag cgcggctatc gtggctggcc acgacgggcg    3060
ttccttgcgc agctgtgctc gacgttgtca ctgaagcggg aagggactgg ctgctattgg    3120
gcgaagtgcc ggggcaggat ctcctgtcat ctcaccttgc tcctgccgag aaagtatcca    3180
tcatggctga tgcaatgcgg cggctgcata cgcttgatcc ggctacctgc ccattcgacc    3240
```

```
accaagcgaa acatcgcatc gagcgagcac gtactcggat ggaagccggt cttgtcgatc    3300
aggatgatct ggacgaagag catcaggggc tcgcgccagc cgaactgttc gccaggctca    3360
aggcgcgcat gcccgacggc gatgatctcg tcgtgaccca tggcgatgcc tgcttgccga    3420
atatcatggt ggaaaatggc cgcttttctg gattcatcga ctgtggccgg ctgggtgtgg    3480
cggaccgcta tcaggacata gcgttggcta cccgtgatat tgctgaagag cttggcggcg    3540
aatgggctga ccgcttcctc gtgctttacg gtatcgccgc tcccgattcg cagcgcatcg    3600
ccttctatcg ccttcttgac gagttcttct gagcgggact ctggggttcg aaatgaccga    3660
ccaagcgacg cccaacctgc catcacgaga tttcgattcc accgccgcct tctatgaaag    3720
gttgggcttc ggaatcgttt ccgggacgcg cggctggatg atcctccagc gcgggatct    3780 catgctggag ttcttcgccc acgggatctc tgcggaacag gcggtcgaag gtgccgatat    3840
cattacgaca gcaacggccg acaagcacaa cgccacgatc ctgagcgaca atatgatcgg    3900
gcccggcgtc cacatcaacg cgtcggcgg cgactgccca ggcaagaccg agatgcaccg    3960
cgatatcttg ctgcgttcgg atattttcgt ggagttcccg ccacgacccc ggatgatccc    4020
cgatcgttca acatttggc aataaagttt cttaagattg aatcctgttg ccggtcttgc    4080
gatgattatc atataatttc tgttgaatta cgttaagcat gtaataatta acatgtaatg    4140
catgacgtta tttatgagat gggttttat gattagagtc ccgcaattat acatttaata    4200
cgcgatagaa acaaaatat agcgcgcaaa ctaggataaa ttatcgcgcg cggtgtcatc    4260
tatgttacta gatcgggcct cctgtcaatg ctggcggcgg ctctggtggt ggttctggtg    4320
gcggctctga gggtggtggc tctgagggtg gcggttctga gggtggcggc tctgagggag    4380
gcggttccgg tggtggctct ggttccggtg attttgatta tgaaaagatg gcaaacgcta    4440 ataaggggc tatgaccgaa aatgccgatg aaaacgcgct acagtctgac gctaaaggca    4500
aacttgattc tgtcgctact gattacggtg ctgctatcga tggtttcatt ggtgacgttt    4560
ccggccttgc taatggtaat ggtgctactg gtgattttgc tggctctaat tcccaaatgg    4620
ctcaagtcgg tgacggtgat aattcacctt taatgaataa tttccgtcaa tatttacctt    4680
ccctccctca atcggttgaa tgtcgccctt ttgtctttgg cccaatacgc aaaccgcctc    4740
tccccgcgcg ttggccgatt cattaatgca gctggcacga caggtttccc gactggaaag    4800
cgggcagtga gcgcaacgca attaatgtga gttagctcac tcattaggca ccccaggctt    4860
tacactttat gcttccggct cgtatgttgt gtggaattgt gagcggataa caatttcaca    4920
caggaaacag ctatgaccat gattacgcca agcttttcaa cgtggtcaga tcatgacgct    4980
tccagaaaac atcgagcaag ctctcaaagc tgatctcttt cggatcgtac tgaacccgaa    5040
caatctcgtt atgccccgtc gtctccgaac agacatcctc gtagctcgga ttgtcgacga    5100
atccatggct atacccaacc tccgtcttcg tcacgccagg aaccctctgg taagccagtt    5160
ccgctcccca gaaacaaccg cgccgaatt gcgcgaattg ctgacctgga dacgaacat    5220 cgtcatcggg tccttgcgcg attgcggcgg aagccgggtc gggttgggga cgagacccga    5280
atccgagcct ggtgaagagg ttgttcatcg agatttgta gactgagatg gatcgagcgg    5340
ttttggggaa agggaagtg ggtttggttt ttttggatag agagtgca gctttggaga    5400 gagactggag aggtttagag agagacgcgg cggagattac cggaggagag gcgacgagag    5460
atagcattat cgaaaggaag ggagaaagag tgacgtggag aaataagaaa cccgttaaga    5520
gtctgatatt tattatatta aaagcccaat gggcctaaac ccatttaaac aagacagata    5580
aatgggccgt gtgttaagtt aacagagtgt taacgttcgg tttcaaatgc caacgccata    5640
```

```
ggaacaaaac aaacgtgtcc tcaagtaaac ccctgccgtt tacacctcaa tggctgcatg    5700
gtgaagccat taacacgtgg cgtaggatgc atgacgacgc cattgacacc tgactctctt    5760
cccttctctt catatatctc taatcaattc aactactcat tgtcatagct attcggaaaa    5820
tacatacaca tccttttctc ttcgatctct ctcaattcgg atccagcaaa gccgccacca    5880
tggctactgc tactgatcgt gcacctcacc aggttcaagt tcacaccccc accacacaac    5940
gcgtcgacgt tccacgccgc ggctacgatg ttagtggtgg tggtattaag actcttctcc    6000
ccgagagagg tccgtccacc tctcaaatca tcgccgtcct cgtcggcgtc cccactgggg    6060
gcactctgtt gctcctctcc ggcctttcac ttctcggaac cataatcggg ctggcaattg    6120
ccaccccggt ttttatcttc ttcagcccgg ttatagttcc cgcggtcgtt accattggac    6180
ttgcagtcac tggtattctc acggcgggag catgtggact aaccgggctg atgtctttgt    6240
catggatgat taacttcatc cgacaggtac atgggacgac ggtgccggat cagctggact    6300
cagtgaagcg gcgcatggcg gacatggcgg attacgtggg gcagaagaca aaggatgctg    6360
gccaagagat acagactaag gcccaggatg ttaagaggtc atcatcactg gtcccaaggg    6420
gtagcgatga accaccgcag tctccatggg ataggggtgaa agatctggcg actgtgtatg    6480
ttgacgtgtt gaaggattct ggcagagatt acgtctctca gtttgaaggt tccgcactcg    6540
ggaagcaact aaatcttaaa cttttggata actgggacag tgtaacaagt acgttctcga    6600
agctgcgaga acagctcggc ccggtgaccc aagaattctg ggataacctt gaaaagaaa    6660 ccgagggtct caggcaagag atgtccaagg acttagagga ggttaaagct aaagttcagc    6720
cttatttgga tgactttcag aaaaagtggc aggaggaaat ggagttgtac cgccaaaaag    6780
ttgaacccct tagagctgag ttgcaagagg gtgcacgcca aagttacac gagttacaag    6840 aaaagctctc accctttgga gaggagatga gagacagggc gcgtgcgcat gtagatgcct    6900
tgcgtactca tcttgctcca tattctgatg aattgagaca atgtcttgct gcacgtctgg    6960
aagccttaaa ggaaaatggg ggagcacggc tagctgagta tcatgctaaa gcaaccgagc    7020
accttagcac tctttcggaa aaggccaaac ccgctttaga agatctacga caaggactcc    7080
tacctgtttt ggaatcattt aaggttagtt tcctctcagc ccttgaagaa tacacaaaga    7140
aacttaacac acaataagag ctcgaatttc cccgatcgtt caaacatttg caataaagt    7200 ttcttaagat tgaatcctgt tgccggtctt gcgatgatta tcatataatt tctgttgaat    7260
tacgttaagc atgtaataat taacatgtaa tgcatgacgt tatttatgag atgggttttt    7320
atgattagag tcccgcaatt atacatttaa tacgcgatag aaaacaaaat atagcgcgca    7380
aactaggata aattatcgcg cgcggtgtca tctatgttac tagatcggga attcactggc    7440
cgtcgtttta caacgtcgtg actgggaaaa ccctggcgtt acccaactta atcgccttgc    7500
agcacatccc cctttcgcca gctggcgtaa tagcgaagag gcccgcaccg atcgcccttc    7560
ccaacagttg cgcagcctga atggcgcccg ctcctttcgc tttcttccct tcctttctcg    7620
ccacgttcgc cggctttccc cgtcaagctc taaatcgggg gctcccttta gggttccgat    7680
ttagtgcttt acggcacctc gaccccaaaa aacttgattt gggtgatggt tcacgtagtg    7740
ggccatcgcc ctgatagacg gttttcgcc ctttgacgtt ggagtccacg ttctttaata    7800
gtggactctt gttccaaact ggaacaacac tcaaccctat ctcgggctat tcttttgatt    7860
tataagggat tttgccgatt tcggaaccac catcaaacag gattttcgcc tgctggggca    7920
aaccagcgtg gaccgcttgc tgcaactctc tcagggccag gcggtgaagg gcaatcagct    7980
```

```
gttgcccgtc tcactggtga aaagaaaaac caccccagta cattaaaaac gtccgcaatg   8040
tgttattaag ttgtctaagc gtcaatttgt ttacaccaca atatatcctg ccaccagcca   8100
gccaacagct ccccgaccgg cagctcggca caaaatcacc actcgataca ggcagcccat   8160
cagtccggga cggcgtcagc gggagagccg ttgtaaggcg gcagactttg ctcatgttac   8220
cgatgctatt cggaagaacg gcaactaagc tgccgggttt gaaacacgga tgatctcgcg   8280
gagggtagca tgttgattgt aacgatgaca gagcgttgct gcctgtgatc aaatatcatc   8340
tccctcgcag agatccgaat tatcagcctt cttattcatt tctcgcttaa ccgtgacagg   8400
ctgtcgatct tgagaactat gccgacataa taggaaatcg ctggataaag ccgctgagga   8460
agctgagtgg cgctatttct ttagaagtga acgttgacga tatcaactcc cctatccatt   8520
gctcaccgaa tggtacaggt cggggacccg aagttccgac tgtcggcctg atgcatcccc   8580
ggctgatcga ccccagatct ggggctgaga aagcccagta aggaaacaac tgtaggttcg   8640
agtcgcgaga tcccccggaa ccaaaggaag taggttaaac ccgctccgat caggccgagc   8700
cacgccaggc cgagaacatt ggttcctgta ggcatcggga ttggcggatc aaacactaaa   8760
gctactggaa cgagcagaag tcctccggcc gccagttgcc aggcggtaaa ggtgagcaga   8820
ggcacgggag gttgccactt gcgggtcagc acggttccga acgccatgga aaccgccccc   8880
gccaggcccg ctgcgacgcc gacaggatct agcgctgcgt ttggtgtcaa caccaacagc   8940
gccacgcccg cagttccgca aatagccccc aggaccgcca tcaatcgtat cgggctacct   9000
agcagagcgg cagagatgaa cacgaccatc agcggctgca cagcgcctac cgtcgccgcg   9060
accccgcccg gcaggcggta gaccgaaata acaacaagc tccagaatag cgaaatatta   9120
agtgcgccga ggatgaagat gcgcatccac cagattcccg ttggaatctg tcggacgatc   9180
atcacgagca ataaacccgc cggcaacgcc cgcagcagca taccggcgac ccctcggcct   9240
cgctgttcgg gctccacgaa aacgccggac agatgcgcct tgtgagcgtc cttggggccg   9300
tcctcctgtt tgaagaccga cagcccaatg atctcgccgt cgatgtaggc gccgaatgcc   9360
acggcatctc gcaaccgttc agcgaacgcc tccatgggct ttttctcctc gtgctcgtaa   9420
acggacccga acatctctgg agctttcttc agggccgaca atcggatctc gcggaaatcc   9480
tgcacgtcgg ccgctccaag ccgtcgaatc tgagccttaa tcacaattgt caattttaat   9540
cctctgttta tcggcagttc gtagagcgcg ccgtgcgtcc cgagcgatac tgagcgaagc   9600
aagtgcgtcg agcagtgccc gcttgttcct gaaatgccag taaagcgctg gctgctgaac   9660
ccccagccgg aactgacccc acaaggccct agcgtttgca atgcaccagg tcatcattga   9720
cccaggcgtg ttccaccagg ccgctgcctc gcaactcttc gcaggcttcg ccgacctgct   9780
cgcgccactt cttcacgcgg gtggaatccg atccgcacat gaggcggaag gtttccagct   9840
tgagcgggta cggctcccgg tgcgagctga aatagtcgaa catccgtcgg gccgtcggcg   9900
acagcttgcg gtacttctcc catatgaatt tcgtgtagtg gtcgccagca aacagcacga   9960
cgatttcctc gtcgatcagg acctggcaac gggacgtttt cttgccacgg tccaggacgc  10020
ggaagcggtg cagcagcgac accgattcca ggtgcccaac gcggtcggac gtgaagccca  10080
tcgccgtcgc ctgtaggcgc gacaggcatt cctcggcctt cgtgtaatac cggccattga  10140
tcgaccagcc caggtcctgg caaagctcgt agaacgtgaa ggtgatcggc tcgccgatag  10200
gggtgcgctt cgcgtactcc aacacctgct gccacaccag ttcgtcatcg tcggcccgca  10260
gctcgacgcc ggtgtaggtg atcttcacgt ccttgttgac gtggaaaatg accttgtttt  10320
gcagcgcctc gcgcgggatt tcttgttgc gcgtggtgaa cagggcagag cgggccgtgt  10380
```

```
cgtttggcat cgctcgcatc gtgtccggcc acggcgcaat atcgaacaag gaaagctgca    10440
tttccttgat ctgctgcttc gtgtgtttca gcaacgcggc ctgcttggcc tcgctgacct    10500
gttttgccag gtcctcgccg gcggtttttc gcttcttggt cgtcatagtt cctcgcgtgt    10560
cgatggtcat cgacttcgcc aaacctgccg cctcctgttc gagacgacgc gaacgctcca    10620
cggcggccga tggcgcgggc agggcagggg gagccagttg cacgctgtcg cgctcgatct    10680
tggccgtagc ttgctggacc atcgagccga cggactggaa ggtttcgcgg ggcgcacgca    10740
tgacggtgcg gcttgcgatg gtttcggcat cctcggcgga aaaccccgcg tcgatcagtt    10800
cttgcctgta tgccttccgg tcaaacgtcc gattcattca ccctccttgc gggattgccc    10860
cgactcacgc cggggcaatg tgcccttatt cctgatttga cccgcctggt gccttggtgt    10920
ccagataatc caccttatcg gcaatgaagt cggtcccgta gaccgtctgg ccgtccttct    10980
cgtacttggt attccgaatc ttgccctgca cgaataccag cgaccccttg cccaaatact    11040
tgccgtgggc ctcggcctga gagccaaaac acttgatgcg gaagaagtcg gtgcgctcct    11100
gcttgtcgcc ggcatcgttg cgccacatct aggtactaaa acaattcatc cagtaaaata    11160
taatatttta ttttctccca atcaggcttg atccccagta agtcaaaaaa tagctcgaca    11220
tactgttctt ccccgatatc ctccctgatc gaccggacgc agaaggcaat gtcataccac    11280
ttgtccgccc tgccgcttct cccaagatca ataaagccac ttactttgcc atctttcaca    11340
aagatgttgc tgtctcccag gtcgccgtgg gaaaagacaa gttcctcttc gggcttttcc    11400
gtctttaaaa aatcatacag ctcgcgcgga tctttaaatg gagtgtcttc ttcccagttt    11460
tcgcaatcca catcggccag atcgttattc agtaagtaat ccaattcggc taagcggctg    11520
tctaagctat tcgtataggg acaatccgat atgtcgatgg agtgaaagag cctgatgcac    11580
tccgcataca gctcgataat cttttcaggg ctttgttcat cttcatactc ttccgagcaa    11640
aggacgccat cggcctcact catgagcaga ttgctccagc catcatgccg ttcaaagtgc    11700
aggacctttg gaacaggcag ctttccttcc agccatagca tcatgtcctt ttcccgttcc    11760
acatcatagg tggtcccttt ataccggctg tccgtcattt ttaaatatag gttttcattt    11820
tctcccacca gcttatatac cttagcagga gacattcctt ccgtatcttt tacgcagcgg    11880 tattttttcga tcagtttttt caattccggt gatattctca ttttagccat ttattatttc    11940
cttcctcttt tctacagtat ttaaagatac cccaagaagc taattataac aagacgaact    12000
ccaattcact gttccttgca ttctaaaacc ttaaatacca gaaaacagct ttttcaaagt    12060
tgttttcaaa gttggcgtat aacatagtat cgacggagcc gattttgaaa ccacaattat    12120
gggtgatgct gccaacttac tgatttagtg tatgatggtg ttttttgaggt gctccagtgg    12180 cttctgtgtc tatcagctgt ccctcctgtt cagctactga cggggtggtg cgtaacggca    12240
aaagcaccgc cggacatcag cgctatctct gctctcactg ccgtaaaaca tggcaactgc    12300
agttcactta caccgcttct caacccggta cgcaccagaa aatcattgat atggccatga    12360
atggcgttgg atgccgggca acagcccgca ttatgggcgt tggcctcaac acgatttttac    12420 gtcacttaaa aaactcaggc cgcagtcggt aacctcgcgc atacagccgg gcagtgacgt    12480
catcgtctgc gcggaaatgg acgaacagtg gggctatgtc ggggctaaat cgcgccagcg    12540
ctggctgttt tacgcgtatg acagtctccg gaagacggtt gttgcgcacg tattcggtga    12600
acgcactatg gcgacgctgg ggcgtcttat gagcctgctg tcacccttttg acgtggtgat    12660 atggatgacg gatggctggc cgctgtatga atcccgcctg aagggaaagc tgcacgtaat    12720
```

```
cagcaagcga tatacgcagc gaattgagcg gcataacctg aatctgaggc agcacctggc   12780
acggctggga cggaagtcgc tgtcgttctc aaaatcggtg gagctgcatg acaaagtcat   12840
cgggcattat ctgaacataa aacactatca ataagttgga gtcattaccc aattatgata   12900
gaatttacaa gctataaggt tattgtcctg ggtttcaagc attagtccat gcaagttttt   12960
atgctttgcc cattctatag atatattgat aagcgcgctg cctatgcctt gccccctgaa   13020
atccttacat acggcgatat cttctatata aaagatatat tatcttatca gtattgtcaa   13080
tatattcaag gcaatctgcc tcctcatcct cttcatcctc ttcgtcttgg tagcttttta   13140
aatatggcgc ttcatagagt aattctgtaa aggtccaatt ctcgtttca tacctcggta    13200 taatcttacc tatcacctca aatggttcgc tgggtttatc gcaccccga acacgagcac    13260 ggcacccgcg accactatgc caagaatgcc caaggtaaaa attgccggcc ccgccatgaa   13320
gtccgtgaat gccccgacgg ccgaagtgaa gggcaggccg ccacccaggc cgccgccctc   13380
actgcccggc acctggtcgc tgaatgtcga tgccagcacc tgcggcacgt caatgcttcc   13440
gggcgtcgcg ctcgggctga tcgcccatcc cgttactgcc ccgatcccgg caatggcaag   13500
gactgccagc gctgccattt ttggggtgag gccgttcgcg gccgaggggc gcagcccctg   13560
gggggatggg aggcccgcgt tagcgggccg ggagggttcg agaaggggg gcacccccct    13620 tcggcgtgcg cggtcacgcg cacagggcgc agccctggtt aaaaacaagg tttataaata   13680
ttggtttaaa agcaggttaa aagacaggtt agcggtggcc gaaaaacggg cggaaaccct   13740
tgcaaatgct ggattttctg cctgtggaca gcccctcaaa tgtcaatagg tgcgcccctc   13800
atctgtcagc actctgcccc tcaagtgtca aggatcgcgc ccctcatctg tcagtagtcg   13860
cgcccctcaa gtgtcaatac cgcagggcac ttatcccag gcttgtccac atcatctgtg    13920
ggaaactcgc gtaaaatcag gcgttttcgc cgatttgcga ggctggccag ctccacgtcg   13980
ccggccgaaa tcgagcctgc ccctcatctg tcaacgccgc gccgggtgag tcggcccctc   14040
aagtgtcaac gtccgcccct catctgtcag tgagggccaa gttttccgcg aggtatccac   14100
aacgccggcg gccgcggtgt ctcgcacacg gcttcgacgg cgtttctggc gcgtttgcag   14160
ggccatagac ggccgccagc ccagcggcga gggcaaccag cccgg                   14205
```

<210> SEQ ID NO 17
<211> LENGTH: 18
<212> TYPE: DNA
<213> ORGANISM: Artificial Sequence
<220> FEATURE:
<223> OTHER INFORMATION: Completely Synthesized

<400> SEQUENCE: 17
atgaactgca ggacgagg                                                     18

<210> SEQ ID NO 18
<211> LENGTH: 18
<212> TYPE: DNA
<213> ORGANISM: Artificial Sequence
<220> FEATURE:
<223> OTHER INFORMATION: Completely Synthesized

<400> SEQUENCE: 18
gcgataccgt aaagcacg                                                     18